(12) United States Patent
Zondlo et al.

(10) Patent No.: US 7,816,102 B2
(45) Date of Patent: Oct. 19, 2010

(54) PROTEIN KINASE-INDUCIBLE DOMAINS

(75) Inventors: Neal J. Zondlo, Newark, DE (US); Shalini Balakrishnan, Newark, DE (US)

(73) Assignee: University of Delaware, Newark, DE (US)

(*) Notice: Subject to any disclaimer, the term of this patent is extended or adjusted under 35 U.S.C. 154(b) by 515 days.

(21) Appl. No.: 11/731,611

(22) Filed: Mar. 30, 2007

(65) Prior Publication Data

US 2007/0243569 A1 Oct. 18, 2007

Related U.S. Application Data

(60) Provisional application No. 60/787,589, filed on Mar. 30, 2006.

(51) Int. Cl.
*C12P 21/06* (2006.01)
*C12Q 1/48* (2006.01)

(52) U.S. Cl. ........................ 435/69.1; 435/15

(58) Field of Classification Search ............... 435/69.1, 435/15
See application file for complete search history.

(56) References Cited

OTHER PUBLICATIONS

Zondlo et al., Abstract, 229th ACS National Meeting, San diego, CA, U.S., Mar. 13-17, 2005.*
Szilak, L. et al., "Design of a Leucine Zipper Coiled Coil Stabilized 1.4 KCAL Mol(-1) . . . ", Protein Science, 1997, 6:1273-1283, Cambridge Univ Press.
Szilak, L. et al., "Phosphorylation Destabilizes a-Helices", Nature Structural Biology, vol. 4, No. 2, Feb. 1997, pp. 112-114, Nature Publishing Group.
Signarvic, R. et al., "De Novo Design of a Molecular Switch: Phosphorylation . . . ", J. Mol. Biol. (2003) 334, pp. 1-12.
Davis, B. et al., "Mimicking Posttranslational Modification of Proteins", Science, Jan. 23, 2004, vol. 303, pp. 480-482.
Babu, Y. et al., "Three-Dimensional Structure of Calmodulin", Nature, vol. 315, May 2, 1985, pp. 37-40, Nature Publishing Group.
Meador, W. et al., "Target Enzyme Recognition by Calmodulin . . . ", Science, vol. 257, Issue 5074, pp. 1251-1255, 1992.
Kuboniwa, H. et al., "Solution Structure of Calcium-Free Calmodulin", Nature Structural Biology, vol. 2, No. 9, Sep. 1995, pp. 768-776.
Wang, C. et al., "Binding of Lanthanide Ions to Troponin C", Biochemistry, 1981, 20, pp. 2439-2444.
Gariepy, J. et al., "Lanthanide-Induced Peptide Folding: Variations in Lanthanide . . . ", Biochemistry, 1983, 22, pp. 1765-1772.
MacManus et at., "Terbium Luminescence in Synthetic Peptide Loops From . . . ", Journal of Biol. Chemistry, vol. 265, No. 18, pp. 10358-10366, 1990.
Siedlecka, M. et al., "a-Helix Nucleation by a Calcium-Binding Peptide Loop", vol. 96, pp. 903-908, Feb. 1999, PNAS USA.
Franz, K. et al., "Lanthanide-Binding Tags As Versatile Protein Coexpression Probes", ChemBioChem, 2003, 4, pp. 265-271, 2003.

Nitz, M. et al., "A Powerful Combinatorial Screen to Identify High-Affinity Terbium . . . ", ChemBioChem, 2003, 4, pp. 272-276.
Selvin, P. et al., "Principles and Biophysical Applications of Lanthanide-Based Probes", Annu. Rev. Biophys. Struct., 2002, 31:275-302.
Barbieri, R. et al., "Paramagnetically Induced Residual Dipolar Couplings for Solution Structure . . . ", J. Am. Chem. Soc., 2002, 124, pp. 5581-5587.
Wohnert, J. et al., "Protein Alignment by a Coexpressed Lanthanide-Binding Tag . . . ", J. Am. Chem. Soc., 2003, 125, pp. 13338-13339.
Kovacic, R. et al., "Sequence-Selective DNA Cleavage by a Chimeric Metallopeptide", J. Am. Chem. Soc., 2003, 125, pp. 6656-6662.
Rothman, D. et al., "Chemical Approaches for Investigating Phosphorylation . . . ", TRENDS in Cell Biology, vol. 15, No. 9, Sep. 2005, pp. 502-510.
Wright, D. et al., "Fluorometric Assay for Adenosine 3', 5'-Cyclic. . . ", vol. 78, No. 10, pp. 6048-6050, Oct. 1981, PNAS USA.
Ng, T. et al., "Imaging Protein Kinase Ca Activation in Cells", Science, vol. 283, Mar. 26, 1999, pp. 2085-2089.
Nagai, Y. et al., "A Fluorescent Indicator for Visualizing cAMP-Induced Phosphorylation in Vivo", Nature Biotechnology, vol. 18, Mar. 2000, pp. 313-316.
Zhang, J. et al., "Genetically Encoded Reporters of Protein Kinase A Activity Reveal Impact . . . ", PNAS, Dec. 18, 2001, vol. 98, No. 26, pp. 14997-15002.
Ting A., et al., "Genetically Encoded Fluorescent Reporters of Protein Tyrosine Kinase . . . ", PNAS, Dec. 18, 2001, vol. 98, No. 26, pp. 15003-15008.
Sato, M. et al., "Fluorescent Indicators for Imaging Protein Phosphorylation in Single Living Cells", Nature Biotechnology, Mar. 2002, vol. 20, pp. 287-294.
Yeh, R., "Real Time Visualization of Protein Kinase Activity in Living Cells", J. Of Biol. Chem., vol. 277, No. 13, pp. 11527-11532, 2002.
Chen, C. et al., "Design and Synthesis of a Fluorescent Reporter of Protein Kinase Activity", J. Am. Chem. Soc., 2002, 124, pp. 3840-3841.
Ojida, A. et al., "First Artificial Receptors and Chemosensors Toward Phosphorylated . . . ", J. Am. Chem. Soc., 2002, 124, pp. 6256-6258.
Veldhuyzen, W. et al., "A Light-Activated Probe of Intracellular Protein Kinase Activity", J. Am. Chem. Soc., 2003, 125, pp. 13358-13359.
Shults, M. et al., "Versatile Fluorescence Probes of Protein Kinase Activity", J. Am. Chem. Soc., 2003, 125, pp. 14248-14249.
Schleifenbaum, A. et al., "Genetically Encoded FRET Probe for PKC Activity Based on Pleckstrin", J. Am. Chem. Soc., 2004, 126, pp. 11786-11787.

(Continued)

*Primary Examiner*—Maryam Monshipouri
(74) *Attorney, Agent, or Firm*—Potter Anderson & Corroon, LLP

(57) ABSTRACT

Applicants have used protein design to develop novel functional protein architectures, termed protein kinase-inducible domains, whose structures are dependent on phosphorylation by specific protein kinases or are dependent on dephosphorylation by specific protein phosphatases. Applicants have designed kinase-inducible domains based on a modular architecture, which allows kinase-inducible domains to be responsive to any specific serine-threonine kinases. Kinase-inducible domains can consist of canonical amino acids, allowing their use as expressible tags of protein kinase activity.

5 Claims, 25 Drawing Sheets

OTHER PUBLICATIONS

Wang, Q. et al., "Phosphorylation-Driven Protein-Protein Interactions: A Protein Kinase . . . ", J. Am. Chem. Soc., 2005, 127, pp. 7684-7685.

Nelson, M. et al., "Structures of EF-Hand Ca2+–Binding Proteins:Diversity in the Organization . . . ", BioMetals, vol. 11, 1998, pp. 297-318.

Rigden, D. et al., "The DxDxDG Motif for Calcium Binding:Multiple Structural . . . ", J. Mol. Biol. (2004) 343, pp. 971-984.

Nitz, M. et al., "Structural Origin of the High Affinity of a Chemically Evolved . . . ", Angew. Chem. Int. Ed., 2004, 43, pp. 3682-3685.

Shults, M. et al., "A Multiplexed Homogeneous Fluorescence-Based Assay . . . ", Nature Methods, 2005, 4pp. 1-7.

Pearson, R. et al., Methods Enzymol., 1991, 200, pp. 62-81.

Cotton, G. et al., "Generation of a Dual-Labeled Fluorescence Biosensor for CRK-III . . . ", Chemistry & Biology 2000, vol. 7, No. 4, pp. 253-261.

\* cited by examiner

A.

B.

EF Hand    DKNADGYIDAAELK pKID-PKA   DKNADGWIDRASLA pKID-PKC   DKNADGWIDAASLK pKID-Erk   DKNADGWIDAASPA (a) Co-injection of phosphorylated and non-phosphorylated pKID-PKA (b) Enzymatic reaction of pKID-PKA with Protein Kinase A

Fig. 24

| Sequence | SEQ ID |
|---|---|
| Ac-DKNADGWIDRASLA-NH$_2$ | (SEQ ID NO:1) |
| Ac-DKNADGWIDAASLK-NH$_2$ | (SEQ ID NO:3) |
| Ac-DKNADGWIDAASPA-NH$_2$ | (SEQ ID NO:5) |
| Ac-DKNADGWIDRRSIIAK-NH$_2$ | (SEQ ID NO:8) |
| Ac-DKNADGWIRRRSIIAK-NH$_2$ | (SEQ ID NO:9) |
| Ac-DADADGWIRRRSIIAK-NH$_2$ | (SEQ ID NO:10) |
| Ac-DANADGWIRRRSIIAK-NH$_2$ | (SEQ ID NO:11) |
| Ac-DANADGWIRRASIIAK-NH$_2$ | (SEQ ID NO:12) |
| Ac-DADADGWIKKASIIAK-NH$_2$ | (SEQ ID NO:13) |
| Ac-DADADGWIRRASIIAK-NH$_2$ | (SEQ ID NO:14) |
| Ac-DKDADGWIRRASIIAK-NH$_2$ | (SEQ ID NO:15) |
| Ac-DADADGWRSRRSIIAK-NH$_2$ | (SEQ ID NO:16) |
| Ac-DKNADGWISRGSFRRKA-NH$_2$ | (SEQ ID NO:17) |
| Ac-DKNADGWISPLSPGPK-NH$_2$ | (SEQ ID NO:18) |
| Ac-YIDKDADGWIRRASIIAK-NH$_2$ | (SEQ ID NO:19) |
| Ac-YIDKDADGWIRRASLLAK-NH$_2$ | (SEQ ID NO:20) |
| Ac-WIDKDADGWIRRASLLAK-NH$_2$ | (SEQ ID NO:21) |
| Ac-DKDADGWISRGSFRRKA-NH$_2$ | (SEQ ID NO:22) |
| Ac-YIDKDADGWISRGSFRRKA-NH$_2$ | (SEQ ID NO:23) |
| Ac-WIDKDADGWISRGSFRRKA-NH$_2$ | (SEQ ID NO:24) |
| Ac-DKDADGWISPLSPGPK-NH$_2$ | (SEQ ID NO:25) |
| Ac-YIDKDADGWISPLSPGPK-NH$_2$ | (SEQ ID NO:26) |
| Ac-WIDKDADGWISPLSPGPK-NH$_2$ | (SEQ ID NO:27) |
| Ac-DADADGWISRRSIIAK-NH$_2$ | (SEQ ID NO:28) |
| Ac-DLNADGWISFRRKA-NH$_2$ | (SEQ ID NO:29) |
| Ac-DLNADGWITAATAK-NH$_2$ | (SEQ ID NO:30) |
| Ac-DLNADGWITAATAK-NH$_2$ | (SEQ ID NO:31) |
| Ac-DLNADGWIT-NH$_2$ | (SEQ ID NO:32) |
| Ac-DKDADGWIRRSSWRVVS-NH$_2$ | (SEQ ID NO:33) |
| Ac-DKDADGWIRRSTWRVVS-NH$_2$ | (SEQ ID NO:34) |
| Ac-DKDADGWRSSMSFASN-NH$_2$ | (SEQ ID NO:35) |

Fig. 24 Contd.

Ac-DKDADGWIS-NH$_2$ (SEQ ID NO:36)

Ac-DKDADGWITFRRKA-NH$_2$ (SEQ ID NO:37)

Ac-DKDGDRWISIIAK-NH$_2$ (SEQ ID NO:38)

Ac-DKDADRWRSIIAK-NH$_2$ (SEQ ID NO:39)

Ac-DKDADGWISPRARSNpSWSKQ-NH$_2$ (SEQ ID NO:40)

Ac-DKDADGWISPRARHApSGAQA-NH$_2$ (SEQ ID NO:41)

US 7,816,102 B2

PROTEIN KINASE-INDUCIBLE DOMAINS

CROSS-REFERENCE TO RELATED APPLICATION

This application claims the benefit of U.S. Provisional Application No. 60/787,589, filed Mar. 30, 2006, incorporated herein by reference in its entirety.

FIELD OF THE INVENTION

Disclosed herein are methods related to the production of protein kinase-inducible and/or protein phosphatase-inducible domains in an amino acid sequence.

BACKGROUND OF THE INVENTION

Reversible phosphorylation of protein hydroxyl groups is a ubiquitous signaling mechanism that renders a limited set of genes capable of cellular specialization and differentiation. In humans, at least 518 genes encode protein kinases and over 100 genes encode protein phosphatases, in total accounting for approximately 2.5% of all human genes [1]. Protein phosphorylation is central to cellular regulation with roles in, for example, cell signaling, signal transduction, and mitosis. Changes in protein phosphorylation states and kinase activity are also associated with many human diseases, most notably cancer, Alzheimer's disease, and heart disease [1-2].

A major class of emerging pharmaceuticals are kinase inhibitors, which typically are small molecules that block the actions of kinases (e.g., Gleevec® (imatinib mesylate) used in cancer treatments; VX-680, an Aurora kinase inhibitor in clinical trial; Herceptin® (trastuzumab), for treatment of breast cancer; Avastin® (bevacizumab), for treatment of metastatic colorectal cancer; Iressa® (gefitinib) and Erbitux® (cetuximab), for treatment of lung and colorectal cancer; everolimus, for treatment of Metastatic Breast Cancer). The vast majority of kinase inhibitor pharmaceuticals or compounds in clinical trial are tyrosine kinase inhibitors; thus, a need exists for identifying and developing novel inhibitors of serine and threonine kinases, which play important roles in cellular and extracellular functions.

Protein phosphorylation is thus a critical regulatory strategy. New tools are necessary which may be used to interrogate and are responsive to the activities of protein kinases and phosphatases.

SUMMARY OF THE INVENTION

Applicants have used protein design to develop a protein motif whose structure is dependent on its phosphorylation state. Previous designs of phosphorylation-dependent protein structure have involved stabilization of alpha-helices or multimeric helical bundles via electrostatic, helix dipole or helix capping interactions [3-5]. Applicants chose to focus on the design of a monomeric protein motif that undergoes a phosphorylation-dependent structural change.

One aspect relates to a method of producing a phosphorylation-dependent protein domain comprising:
(a) replacing a structurally significant glutamic acid or aspartic acid residue in a polypeptide with a serine or threonine residue; and
(b) optionally, activating the domain comprising the replacement serine or threonine residue by phosphorylating the serine or threonine residue.

Another aspect relates to an isolated polypeptide comprising an EF hand domain, wherein the EF hand domain has a structurally significant glutamic acid or aspartic acid residue substituted with a serine or threonine residue.

A further aspect is for a method of identifying protein kinase activity comprising:
(a) providing a host cell with a polypeptide comprising a protein kinase-inducible domain having a structurally significant glutamic acid or aspartic acid residue replaced with a serine or threonine residue; and
(b) identifying protein kinase activity by detecting phosphorylation of the replaced serine or threonine residue.

Another aspect is for a method of identifying protein phosphatase activity comprising:
(a) providing a host cell with a polypeptide comprising a protein phosphatase-inducible domain having a structurally significant glutamic acid or aspartic acid residue replaced with a phosphoserine or phosphothreonine residue; and
(b) identifying protein phosphatase activity by detecting dephosphorylation of the replaced phosphoserine or phosphothreonine residue.

A further aspect relates to a method of screening for protein kinase inhibitor comprising:
(a) providing a host cell with a polypeptide comprising a protein kinase-inducible domain having a structurally significant glutamic acid or aspartic acid residue replaced with a serine or threonine residue;
(b) introducing into the host cell a test compound;
(c) activating in the host cell a protein kinase which recognizes the protein kinase-inducible domain; and
(d) measuring the phosphorylation of the replaced serine or threonine residue;

whereby inhibition of phosphorylation of the replaced serine or threonine residue is indicative of the test compound being a protein kinase inhibitor.

An additional aspect relates to a method of screening for a protein phosphatase inhibitor comprising:
(a) providing a host cell with a polypeptide comprising a protein phosphatase-inducible domain having a structurally significant glutamic acid or aspartic acid residue replaced with a phosphoserine or phosphothreonine residue;
(b) introducing into the host cell a test compound;
(c) activating in the host cell a protein phosphatase which recognizes the protein phosphatase-inducible domain; and
(d) measuring the phosphorylation of the replaced phosphoserine or phosphothreonine residue;

whereby inhibition of dephosphorylation of the replaced phosphoserine or phosphothreonine residue is indicative of the test compound being a protein phosphatase inhibitor.

A further aspect is for a method of identifying protein kinase activity comprising:
(a) providing a polypeptide comprising a protein kinase-inducible domain having a structurally significant glutamic acid or aspartic acid residue replaced with a serine or threonine residue;
(b) contacting the polypeptide of (a) with a suspected protein kinase; and
(c) detecting phosphorylation of the serine or threonine residue of the polypeptide of (a).

An additional aspect relates to a method of identifying protein phosphatase activity comprising:
(a) providing a polypeptide comprising a protein kinase-inducible domain having a structurally significant glutamic acid or aspartic acid residue replaced with a phosphoserine or phosphothreonine residue;

(b) contacting the polypeptide of (a) with a suspected protein phosphatase; and (c) detecting dephosphorylation of the serine or threonine residue of the polypeptide of (a).

Another aspect is for a method of screening for a protein kinase inhibitor comprising:

(a) providing a polypeptide comprising a protein kinase-inducible domain having a structurally significant glutamic acid or aspartic acid residue replaced with a serine or threonine residue;

(b) contacting the polypeptide of (a) with:
  (1) a protein kinase having a kinase recognition domain on polypeptide of (a) and
  (2) a test compound suspected of being a kinase inhibitor; and (c) detecting phosphorylation of the serine or threonine residue of the polypeptide of (a), whereby inhibition of phosphorylation of the replaced serine or threonine residue is indicative of the test compound being a protein kinase inhibitor.

A further aspect relates to a method of screening for a protein phosphatase inhibitor comprising:

(a) providing a polypeptide comprising a protein kinase-inducible domain having a structurally significant glutamic acid or aspartic acid residue replaced with a phosphoserine or phosphothreonine residue;

(b) contacting the polypeptide of (a) with:
  (1) a protein phosphatase having a phosphatase recognition domain on polypeptide of (a) and
  (2) a test compound suspected of being a phosphatase inhibitor; and (c) detecting phosphorylation of the phosphoserine or phosphothreonine residue of the polypeptide of (a), whereby inhibition of dephosphorylation of the replaced phosphoserine or phosphothreonine residue is indicative of the test compound being a protein phosphatase inhibitor.

Other objects and advantages will become apparent to those skilled in the art upon reference to the detailed description that hereinafter follows.

BRIEF DESCRIPTION OF THE SEQUENCES

SEQ ID NO:1 represents an EF hand domain having a glutamic acid residue at position 12 replaced with a serine residue and having a protein kinase A recognition domain.

SEQ ID NO:2 represents the EF hand domain of SEQ ID NO:1 with the serine residue phosphorylated.

SEQ ID NO:3 represents an EF hand domain having a glutamic acid residue at position 12 replaced with a serine residue and having a protein kinase C recognition domain.

SEQ ID NO:4 represents the EF hand domain of SEQ ID NO:3 with the serine residue phosphorylated.

SEQ ID NO:5 represents an EF hand domain having a glutamic acid residue at position 12 replaced with a serine residue and having an Erk recognition domain.

SEQ ID NO:6 represents the EF hand domain of SEQ ID NO:5 with the serine residue phosphorylated.

SEQ ID NO:7 represents a consensus EF hand domain.

SEQ ID NOs: 8-41 represent protein kinase-inducible EF hand domains. SEQ ID NOs: 29, 31, 32, and 36-39 have the serine or threonine residue at residue 9 rather than residue 12. SEQ ID NOs: 40 and 41 have the serine residue at position number 16 phosphorylated.

BRIEF DESCRIPTION OF THE FIGURES

FIG. 24. Protein kinase-inducible EF hand domains.

DETAILED DESCRIPTION OF THE INVENTION

Applicants specifically incorporate the entire content of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Protein Kinase-Inducible and/or Protein Phosphatase-Inducible Domains

Figure 2:
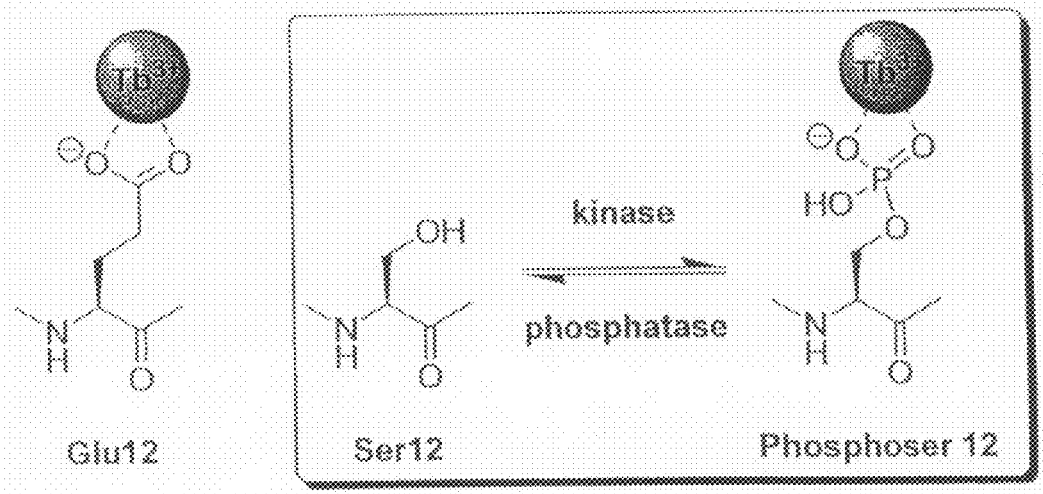
FIG. 2. Design of a phosphorylation-dependent motif, indicating roles of glutamic acid, serine, and phosphoserine residues.

The key design element is the use of phosphoserine or phosphothreonine, preferably phosphoserine, as an inducible mimic of a structurally significant glutamic acid or aspartic acid residue, preferably a glutamic acid residue. By "structurally significant" is meant that the glutamic acid or aspartic acid residue plays an important role in the secondary, tertiary, and/or quaternary structure of a peptide. Phosphoserine and glutamic acid are approximately isosteric anions, suggesting that the replacement of glutamic acid with phosphoserine would generate a motif that would bind metal in a phosphorylation-dependent manner (see, e.g., FIG. 2). Indeed, glutamic acid is commonly used as a mimic of phosphoserine [6]. Here, Applicants employed an inverse approach, in which phosphoserine, but not serine, mimics the electrostatic and Lewis base properties of glutamic acid.

In one embodiment, a designed phosphorylation-dependent protein domain (a) exhibits complete structural switching upon phosphorylation; (b) includes a protein kinase recognition sequence; (c) comprises a modular motif that is compatible with different protein kinase recognition sequences; (d) includes a fluorescent reporter element for readout; and (e) consists entirely of canonical amino acids, to enable its use as a genetically encoded phosphorylation-dependent protein tag and as a building block in the design of larger phosphorylation-dependent protein architectures.

This strategy can be applied, in one embodiment, to the design of phosphorylation-dependent EF hand domains. The term "EF hand" refers to a protein domain containing a simple calcium-binding motif in which the metal is bound by five side chain groups and one main carbonyl (see FIG. 1). EF hand proteins, such as, for example, calmodulin, undergo a significant conformational change to a well-folded helix-loop-helix structure upon calcium binding [7-9]. Due to similar electronics and ionic radii of calcium and lanthanides, EF hands effectively coordinate lanthanides [10-16], thereby endowing the EF hand with the luminescent, magnetic, and hydrolytic properties of lanthanides [17-20].

The EF hand motif accommodates a wide range of residues at most positions. In contrast, residue 12 of the EF hand is nearly invariantly glutamic acid, which binds the metal in a bidentate manner. Replacement of glutamic acid with phosphoserine generates a motif that binds metal in a phosphorylation-dependent manner (See FIG. 2). Non-phosphorylated serine is a poor glutamic acid mimic and should poorly bind metal; in contrast, serine phosphorylation should lead to a tight protein-metal complex. Critically, residues N-terminal and C-terminal to residue 12 are poorly conserved across EF hand proteins, and thus may be tuned to incorporate the recognition sequence of a protein serine/threonine kinase of interest [21]. In other embodiments of the EF-hand, glutamic acid or aspartic acid residues bind from different positions, including residue 9, residue 16, or from a different position in the tertiary or quaternary quaternary structure of the protein [46-47].

In one aspect, an inducible EF hand domain can be defined by the following formula:

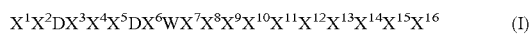
$$X^1X^2DX^3X^4X^5DX^6WX^7X^8X^9X^{10}X^{11}X^{12}X^{13}X^{14}X^{15}X^{16} \quad (I)$$

wherein $X^1$ is an optionally present amino acid;
$X^2$ is an optionally present amino acid;
$X^3$ is any amino acid, preferably K, A, or L;
$X^4$ is any amino acid, preferably N or D;
$X^5$ is A or G;
$X^6$ is any amino acid, preferably G or R
$X^7$ is any amino acid, preferably I or R;
$X^8$ is any amino acid, preferably D, R, S, or T;
$X^9$ is any amino acid, preferably A, R, K, P, or F;
$X^{10}$ is an optionally present amino acid, preferably A, R, G, or L, provided that, when $X^8$ is not S or T, $X^{10}$ is present;
$X^{11}$ is an optionally present amino acid, preferably S, T, or R, provided that, when $X^8$ is not S or T, $X^{11}$ is present and is S or T;
$X^{12}$ is an optionally present amino acid, preferably L, P, I, K, or F;
$X^{13}$ is an optionally present amino acid, preferably K, A, I, R, G, or L;
$X^{14}$ is an optionally present amino acid, preferably A, R, or P;
$X^{15}$ is an optionally present amino acid, preferably K;
$X^{16}$ is an optionally present amino acid, preferably A.

For formula I, standard polypeptide abbreviations for amino acid residues are used, as shown in Table 1.

TABLE 1

| 1-Letter Code | 3-Letter Code | Amino Acid |
|---|---|---|
| A | Ala | Alanine |
| C | Cys | Cysteine |
| D | Asp | Aspartic Acid |
| E | Glu | Glutamic Acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |

TABLE 1-continued

| 1-Letter Code | 3-Letter Code | Amino Acid |
|---|---|---|
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

The EF hand domain can have the amino acid sequence set forth in SEQ ID NO:1, SEQ ID NO:3, SEQ ID NO:5, SEQ ID NO:8, SEQ ID NO:9, SEQ ID NO:10 SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, or SEQ ID NO:39; can have the amino acid sequence set forth in SEQ ID NO:2, SEQ ID NO:4, or SEQ ID NO:6 (when the serine residue is phosphorylated); or can have the amino acid sequence set forth in SEQ ID NO:40 or SEQ ID NO:41 wherein the serine at amino acid residue number 16 is phosphorylated.

Effectiveness of inducible EF domains can be optimized through electrostatic balance of the EF domain between the N-terminal and C-terminal region. For example, modification of an EF hand domain to accommodate a consensus PKA recognition sequence in the C-terminal region of the EF hand typically changes the electrostatic balance of the EF hand domain towards a positive charge due mainly to the change of neutral or negatively-charge amino acids to positive ones (especially to arginines). By electrostatically balancing the inducible EF hand domain through the modification of N-terminal amino acids to negatively-charged amino acids or through the addition of negatively-charged amino acids N-terminal of the EF hand domain, inducible functioning as described herein is increased as compared to electrostatically unbalanced EF hand domains.

In embodiments where expressibility in cells is desired, the amino acids of the protein kinase-inducible domain can be canonical. This flexibility in domain composition is advantageous over known kinase assays where detectability of kinase activity is dependent on the use of non-canonical and/or synthetic amino acids that cannot be produced via a cell-based expression system. The protein kinase-inducible domains disclosed herein, however, can readily be produced via any expression as would be known to one of ordinary skill in the art. Of course, non-canonical and/or synthetic amino acids can be utilized in the connection with the presently disclosed protein-kinase inducible domains in embodiments where cellular expressibility is not needed or undesired.

Provided that a proper kinase recognition sequence is present in the phosphorylation-dependent protein domain, any serine/threonine kinase should be functional in connection with the disclosed phosphorylation-dependent protein domains. Exemplary serine/threonine kinases include protein kinase A, protein kinase C, protein kinase G, calmodulin-dependent protein kinases (e.g., CaMKI, II, III, IV, V), casein kinases (e.g., CKI, II), cyclin-dependent kinases (e.g., CDK1-12), Jun N-terminal kinases (e.g., JNK1-14), MAP kinases (e.g., Erk, p38, RAF, ASK), myosin light chain kinase, Akt/protein kinase Bs (e.g., Akt1-3), G protein-coupled receptor kinases (e.g., GRK1-7), glycogen synthase kinases (e.g., GSK1-5), p21-activated kinases (e.g., PAK1-7), serum- and glucocorticoid-induced kinases (e.g., SGK1-3), 14-3-3 proteins (e.g., 14-3-3α, β, γ, δ, ε, ζ), AMP kinases (e.g., AMPK1-2), Aurora A Kinase, Aurora B Kinase, checkpoint kinases (e.g., Chk1-4), cytosolic protamine kinase, NEMO-like kinase, NIMA-related kinases (e.g., NEK1-12), phosphoinositide-dependent protein kinases (e.g., PDK1-4), Pim kinases (e.g., Pim1-6), receptor interacting protein kinases (e.g., RIPK1-5), Rho-associated kinase (e.g., ROCK1-3), S6 kinases (e.g., p70 S6 kinase, RSK1-6), STE family kinases (e.g., STK1-6), thousand and one amino acid protein kinases (e.g., TAO1-3), ZIP kinase. One of ordinary skill in the art can readily identify the recognition sequences for the aforementioned serine/threonine kinases and can thus incorporate said sequences into the phosphorylation-dependent protein domains disclosed herein to provide the desired serine/threonine kinase specificity.

It is also contemplated that protein phosphatase-inducible domains are within the scope of the present disclosure. Useful protein phosphatases include, for example, PP1, PP2A-D, PP3, PP4, PP5, PP6. One of ordinary skill in the art can readily identify the recognition sequences for the aforementioned protein phosphatases and can thus incorporate said sequences into the phosphorylation-dependent protein domains disclosed herein to provide the desired protein phosphatase specificity.

In addition to EF hand domains, other protein kinase-inducible and/or protein phosphatase-inducible domains are also possible so long as the domain contains a structurally significant glutamic acid or aspartic acid residue. For example, a zinc finger domain can be redesigned to bind terbium or other lanthanide metals, with metal binding by aspartic acid or glutamic acid residues. Replacement of one or more of these aspartic acid or glutamic acid residues with phosphoserine or phosphothreonine. This domain may function as a protein kinase-inducible and/or protein phosphatase-inducible domain.

Phosphorylation-Dependent Protein Domain Polypeptides and Polynucleotides

A phosphorylation-dependent protein domain comprising a glutamic acid or aspartic acid residue replaced with a serine or threonine residue can be produced by any technique known in the art to synthesize polypeptides. Techniques for chemical synthesis of polypeptides are well known in the art (see, e.g., [22]). Examples of techniques for biochemical synthesis involving the introduction of a nucleic acid into a cell and expression of nucleic acids are also well known in the art (see, e.g., [23-24]). Another exemplary technique, described in U.S. Pat. No. 5,304,489, incorporated herein by reference, is the use of transgenic mammals having mammary gland-targeted mutations which result in the production and secretion of synthesized peptides in the milk of the transgenic mammal.

A further aspect is for isolated nucleotide sequences which encode amino acid sequences comprising the phosphorylation-dependent protein domains described herein. Because of "codon degeneracy", i.e., divergence in the genetic code permitting variation of the nucleotide sequence without affecting the amino acid sequence of an encoded polypeptide, the present disclosure thus relates to any nucleotide sequence that encodes an amino acid sequence comprising, consisting essentially of, or consisting of a phosphorylation-dependent protein domain described herein, for example as set forth in the amino acid sequences disclosed herein. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

Also contemplated are isolated nucleotide sequences complementary to the nucleotide sequences which encode the phosphorylation-dependent protein domains described herein.

Expression of a nucleotide sequence may be accomplished by first constructing a chimeric gene in which a coding region is operably linked to at least one promoter capable of directing expression of the gene. For convenience, the chimeric gene may comprise promoter sequences and translation leader sequences derived from the same genes. 3' non-coding sequences encoding transcription termination signals should also be provided. The instant chimeric gene may also comprise one or more introns in order to facilitate gene expression.

A plasmid vector comprising the instant chimeric gene can then be constructed. The choice of plasmid vector is dependent upon the method that will be used to transfect host cells. The skilled artisan is well aware of the genetic elements that must be present on the plasmid vector in order to successfully transform, select, and propagate host cells containing the chimeric gene. The skilled artisan will also recognize that different independent transformation events will result in different levels and patterns of expression (see, e.g., [25-26]), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications, it may be useful to direct the amino acid sequence comprising, consisting essentially of, or consisting of a phosphorylation-dependent protein domain to different cellular compartments or to facilitate its secretion from the cell. Therefore, the chimeric gene described above may be further supplemented by altering the coding sequences to encode the amino acid sequence comprising, consisting essentially of, or consisting of a phosphorylation-dependent protein domain with appropriate intracellular targeting sequences such as transit sequences [27], signal sequences or sequences encoding endoplasmic reticulum localization [28], or nuclear localization signals [29] added and/or with targeting sequences that are already present removed. While the references cited give examples of each of these, the list is not exhaustive and, thus, other targeting signals of utility may be useful in connection with the present disclosure.

Genetically-Encoded Tags of Protein Kinase Activity

In one embodiment, the kinase-inducible domain peptides disclosed herein comprise an expressible sequence, potentially enabling their use as genetically encoded tags of protein kinase activity. In one aspect, the design comprises an EF hand consensus sequence, a tryptophan at residue 9 of formula (I) to sensitize lanthanide luminescence, and a recognition sequence of a serine/threonine kinase. The EF hand domain can, e.g., have the amino acid sequence set forth in SEQ ID NO:1, SEQ ID NO:3, SEQ ID NO:5, SEQ ID NO:8, SEQ ID NO:9, SEQ ID NO:10 SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, or SEQ ID NO:41. The sequences, including several sequences in series, can be incorporated as an N-terminal or C-terminal extension to an encoded protein sequence, on a plasmid or stably incorporated into a host genome. In one example, the sequence is incorporated as a fusion protein as a C-terminal sequence on glutathione S-transferase. In another example, the sequence is incorporated as a fusion protein as a C-terminal sequence on green fluorescence protein. In another example, the sequence is incorporated as a fusion protein with c-jun, to enable subcellular targeting of the protein kinase-inducible domain.

Screening Assays

According to another aspect, methods of screening for kinase activity are provided. One method of identifying protein kinase activity relates to a cell-based assay comprising (a) providing a host cell with a polypeptide comprising a protein kinase-inducible domain having a structurally significant glutamic acid or aspartic acid residue replaced with a serine or threonine residue; and (b) identifying protein kinase activity by detecting phosphorylation of the replaced serine or threonine residue. In one embodiment, the host cell is transfected with a polynucleotide encoding the polypeptide comprising a protein kinase-inducible domain having a structurally significant glutamic acid or aspartic acid residue replaced with a serine or threonine residue. Transfection methods are well known to those of ordinary skill in the art. In another embodiment, the polypeptide comprising a protein kinase-inducible domain having a structurally significant glutamic acid or aspartic acid residue replaced with a serine or threonine residue is inserted into the host cell by any method as known in the art, e.g., by injection or liposomal delivery.

The host cell can be, for example, of mammalian origin, preferably of human origin.

Suitable methods of kinase activity detection are disclosed elsewhere herein. Additionally, other kinase activity detection methods are well known to those of ordinary skill in the art.

Cell-based methods of screening for phosphatase activity are also provided. One method of identifying protein phosphatase activity comprises (a) providing a host cell with a polypeptide comprising a protein phosphatase-inducible domain having a structurally significant glutamic acid or aspartic acid residue replaced with a phosphoserine or phosphothreonine residue; and (b) identifying protein phosphatase activity by detecting dephosphorylation of the replaced phosphoserine or phosphothreonine residue.

Cell-free assays can also be utilized to identify kinase or phosphatase activity. One aspect thus relates to a method of identifying protein kinase activity comprising: (a) providing a polypeptide comprising a protein kinase-inducible domain having a structurally significant glutamic acid or aspartic acid residue replaced with a serine or threonine residue; (b) contacting the polypeptide of (a) with a suspected protein kinase; and (c) detecting phosphorylation of the serine or threonine residue of the polypeptide of (a). Another aspect relates to a method of identifying protein phosphatase activity comprising: (a) providing a polypeptide comprising a protein kinase-inducible domain having a structurally significant glutamic acid or aspartic acid residue replaced with a phosphoserine or phosphothreonine residue; (b) contacting the polypeptide of (a) with a suspected protein phosphatase; and (c) detecting dephosphorylation of the serine or threonine residue of the polypeptide of (a).

Another aspect is for screening assays used to identify inhibitors of kinase or phosphatase activity. One embodiment is for a cell-based assay comprising (a) providing a host cell with a polypeptide comprising a protein kinase-inducible domain having a structurally significant glutamic acid or aspartic acid residue replaced with a serine or threonine residue; (b) introducing into the host cell a test compound; (c) activating in the host cell a protein kinase which recognizes the protein kinase-inducible domain; and (d) measuring the phosphorylation of the replaced serine or threonine residue; whereby inhibition of phosphorylation of the replaced serine or threonine residue is indicative of the test compound being a protein kinase inhibitor.

Cell-based assays for identifying phosphatase inhibitors are also provided. One embodiment is for a method of screening for a protein phosphatase inhibitor comprising: (a) providing a host cell with a polypeptide comprising a protein phosphatase-inducible domain having a structurally significant glutamic acid or aspartic acid residue replaced with a phosphoserine or phosphothreonine residue; (b) introducing into the host cell a test compound; (c) activating in the host cell a protein phosphatase which recognizes the protein phosphatase-inducible domain; and (d) measuring the phosphorylation of the replaced phosphoserine or phosphothreonine residue; whereby inhibition of dephosphorylation of the replaced phosphoserine or phosphothreonine residue is indicative of the test compound being a protein phosphatase inhibitor.

Alternatively, cell-free assays can be used to identify kinase or phosphatase inhibitors. One embodiment is for a method of screening for a protein kinase inhibitor comprising: (a) providing a polypeptide comprising a protein kinase-inducible domain having a structurally significant glutamic acid or aspartic acid residue replaced with a serine or threonine residue; (b) contacting the polypeptide of (a) with: (1) a protein kinase having a kinase recognition domain on polypeptide of (a) and (2) a test compound suspected of being a kinase inhibitor; and (c) detecting phosphorylation of the serine or threonine residue of the polypeptide of (a), whereby inhibition of phosphorylation of the replaced serine or threonine residue is indicative of the test compound being a protein kinase inhibitor. Another embodiment is for a method of screening for a protein phosphatase inhibitor comprising: (a) providing a polypeptide comprising a protein kinase-inducible domain having a structurally significant glutamic acid or aspartic acid residue replaced with a phosphoserine or phosphothreonine residue; (b) contacting the polypeptide of (a) with: (1) a protein phosphatase having a phosphatase recognition domain on polypeptide of (a) and (2) a test compound suspected of being a phosphatase inhibitor; and (c) detecting phosphorylation of the phosphoserine or phosphothreonine residue of the polypeptide of (a), whereby inhibition of dephosphorylation of the replaced phosphoserine or phosphothreonine residue is indicative of the test compound being a protein phosphatase inhibitor.

In some embodiments, identification of kinase or phosphatase inhibitors can be accomplished through the use of high-throughput screening assays to screen large number of compounds.

Another aspect pertains to novel inhibitors identified by the above-described screening assays. Accordingly, it is within the scope of this disclosure to use as a kinase or phosphatase inhibitor a compound identified herein.

Other Uses

Protein kinase-inducible domains and/or protein phosphatase-inducible domains bind other metals, including the other lanthanide metals, The metal gadolinium is used in magnetic resonance imaging. The binding of ligands to gadolinium changes the imaging properties of the gadolinium. Binding of gadolinium to peptides and proteins can be assessed by magnetic resonance imaging [48]. Protein kinase-inducible domains and/or protein phosphatase-inducible domains can be used for imaging of kinase activity and/or phosphatase activity by magnetic resonance imaging.

All of the compositions and methods disclosed and claimed herein can be made and executed without undue experimentation in light of the present disclosure. It will be apparent to those of skill in the art that variations may be applied to the compositions and methods and in the steps or in the sequence of steps of the method described herein without departing from the concept, spirit, and scope of the invention. More specifically, it will be apparent that certain agents which are chemically or biologically related may be substituted for the agents described herein while the same or similar results would be achieved. All such similar substitutes and modifications apparent to those skilled in the art are deemed to be within the spirit, scope, and concept of the invention as defined by the appended claims.

EXAMPLES

The present invention is further defined in the following Examples. It should be understood that these Examples are given by way of illustration only. From the above discussion and these Examples, one skilled in the art can ascertain the preferred features of this invention, and without departing from the spirit and scope thereof, can make various changes and modifications of the invention to adapt it to various uses and conditions.

Materials

Amino acids and resins for peptide synthesis were purchased from Novabiochem. HBTU was purchased from Senn Chemicals. Diisopropylethylamine (DIPEA) was purchased from Aldrich. Dimethyl formamide (DMF), methylene chloride, and trifluoroacetic acid (TFA) were purchased from Acros. Other compounds were purchased from Acros unless otherwise indicated. Peptide synthesis was carried out on a Rainin PS3 automated peptide synthesizer. Peptide stock solutions were prepared in ultrapure water purified by a Millipore Synergy 185 water purification system with a Simpak® 2 cartridge. Peptide concentrations were determined by UV NIS based on tryptophan absorbance ($\epsilon$=5690 $M^{-1}$ $cm^{-1}$ at 280 nm in water) on a PerkinElmer Lambda 25 spectrometer. Peptide stock solutions were stored at −10° C. Postsynthetic modification reactions were performed in capped disposable fritted columns (Image Molding). All compounds were used as purchased with no additional purification. Terbium(III) chloride stocks were freshly prepared from hexahydrate salts (Aldrich). 500 mM HEPES buffer pH 7.8 was prepared from HEPES (Acros) and adjusted to pH 7.8 with a 1 M NaOH solution. NaCl (1 M) and $CaCl_2$ (1 M) solutions were prepared from the corresponding salts (Acros).

Peptide Synthesis

Peptides were synthesized using standard Fmoc solid phase peptide synthesis with Rink amide resin (0.25 mmol). The resin was swelled in DMF (5 min) prior to the start of the synthesis. Amino acid couplings were performed using Fmoc amino acids (1 mmol, 4 equiv) and HBTU (1 mmol, 4 equiv). The following steps were used for each cycle of peptide synthesis: (1) removal of the Fmoc group with 20% piperidine in DMF, 3×5 min; (2) resin wash (DMF, 5×1 min); (3) amide coupling (amino acid, HBTU and 0.05 M DIPEA in DMF, 50 min); (4) resin wash (DMF, 3×1 min). Trityl-protected serine was incorporated at the phosphorylation site to allow for site-specific phosphorylation. After addition of the final residue, the N-terminal Fmoc group was removed (20% piperidine in DMF, 3×5 mins) and the amino terminus acetylated (10% acetic anhydride in pyridine, 5 mins). The resin was washed with DMF (6×) and $CH_2Cl_2$ (3×).

Non-phosphorylated peptides were subjected to cleavage from resin and deprotection for 3 h (TFA:thioanisole:ethanedithiol:phenol:water, 84:4:4:4:4). The solutions were concentrated by evaporation under nitrogen and the peptides were precipitated with ether. The precipitate was dissolved in water, the resulting solution was filtered, and the peptides was purified by reverse phase HPLC (Vydac semipreparative C18, 10×250 mm, 5 μm particle size, 300 Å pore) using a linear gradient of 0-40% buffer B (80% MeCN, 20% $H_2O$, 0.05% TFA) in buffer A (98% $H_2O$, 2% MeCN, 0.06% TFA) over 60 minutes. Peptides were purified to homogeneity, as indicated by the presence of a single peak on reinjection on analytical HPLC (Microsorb MV C18, 4.6×250 mm, 3-5 μm particle size, 100 Å pore). Peptides were characterized by ESI-MS (negative icon mode) on an LCQ Advantage (Finnigan) mass spectrometer.

Peptides were chemically phosphorylated on resin by the following procedure: (1) deprotection of the trityl group with 2% TFA/5% triethylsilane (TES)/93% $CH_2Cl_2$, 3×1 min, or until the flow-through solution was clear; (2) phosphorylation was performed under nitrogen by addition to the resin of tetrazole (1.35 mmol; 3 mL of 3% tetrazole solution in MeCN) (Transgenomics) and O,O-dibenzyl-N,N-diisopropylphosphoramidite (500 μL, 1.52 mmol) (Fluka), and allowed to react for 3 h with gentle mixing on a Barnstead-Thermoline Labquake rotary shaker. The solution was removed and the resin washed with DMF (3×) and $CH_2Cl_2$ (3×); (3) oxidation was performed with t-butyl hydroperoxide (2 mL of a 3 M solution in $CH_2Cl_2$) and allowed to react with mixing for 30 mins. The solution was removed and the resin washed with DMF (3×), MeOH (3×), and ether (3×).

The phosphorylated peptides were purified and characterized as described above for non-phosphorylated peptides.

Produced peptides are described in Table 1.

TABLE 1

Characterization data for non-phosphorylated and phosphorylated peptides (pS indicates phosphoserine).

| Peptide | Sequence | Calculated mass | $[M - H]^-$ observed |
|---|---|---|---|
| non-phosphorylated pKID-PKA | Ac-DKNADGWIDRASLA-NH$_2$ (SEQ ID NO:1) | 1571.8 | 1592.8 $[M + Na^+ - 2H]$ |
| phosphorylated pKID-PKA | Ac-DKNADGWIDRApSLA-NH$_2$ (SEQ ID NO:2) | 1651.8 | 1650.6 |
| non-phosphorylated pKID-PKC | Ac-DKNADGWIDAASLK-NH$_2$ (SEQ ID NO:3) | 1543.8 | 1542.8 |
| phosphorylated pKID-PKC | Ac-DKNADGWIDAApSLK-NH$_2$ (SEQ ID NO:4) | 1623.8 | 1622.7 |
| non-phosphorylated pKID-Erk | Ac-DKNADGWIDAASPA-NH$_2$ (SEQ ID NO:5) | 1470.7 | 1469.5 |
| phosphorylated pKID-Erk | Ac-DKNADGWIDAApSPA-NH$_2$ (SEQ ID NO:6) | 1550.7 | 1548.7 |

Fluorescence Experiments

Fluorescence spectra were collected on a Photon Technology International fluorescence spectrometer model QM-3/2003 with a CW source and a Hamamatsu R928 PMT. All experiments were conducted with an excitation wavelength of 280 nm. 6 nm excitation and emission slit widths were used unless otherwise indicated. All spectra were acquired at room temperature, collecting data every 1 nm with a scan rate of 1 nm per second. At least 3 independent binding titrations were conducted for each peptide. All spectra are uncorrected and have not been normalized, and only representative (median), non-averaged spectra are shown, unless otherwise indicated. All fluorescence experiments were conducted using a 495 nm highpass filter (model 495FG03-25 AM-53074; Andover Corporation, Andover, N.H.) on the emission monochromator.

Peptide solutions were prepared by dilution of stock solutions into 5 mM HEPES buffer (pH 7.8) with 100 mM NaCl. Spectra were acquired in 10 mm quartz fluorescence cells (Starna). $Tb^{3+}$ titrations were conducted by dilution of a $Tb^{3+}$ solution into a peptide solution as described above. Each individual emission spectrum represents an independently prepared solution of peptide and metal. The $Tb^{3+}$ emission band at 544 nm was used to evaluate metal binding.

Example 1

Figure 1:
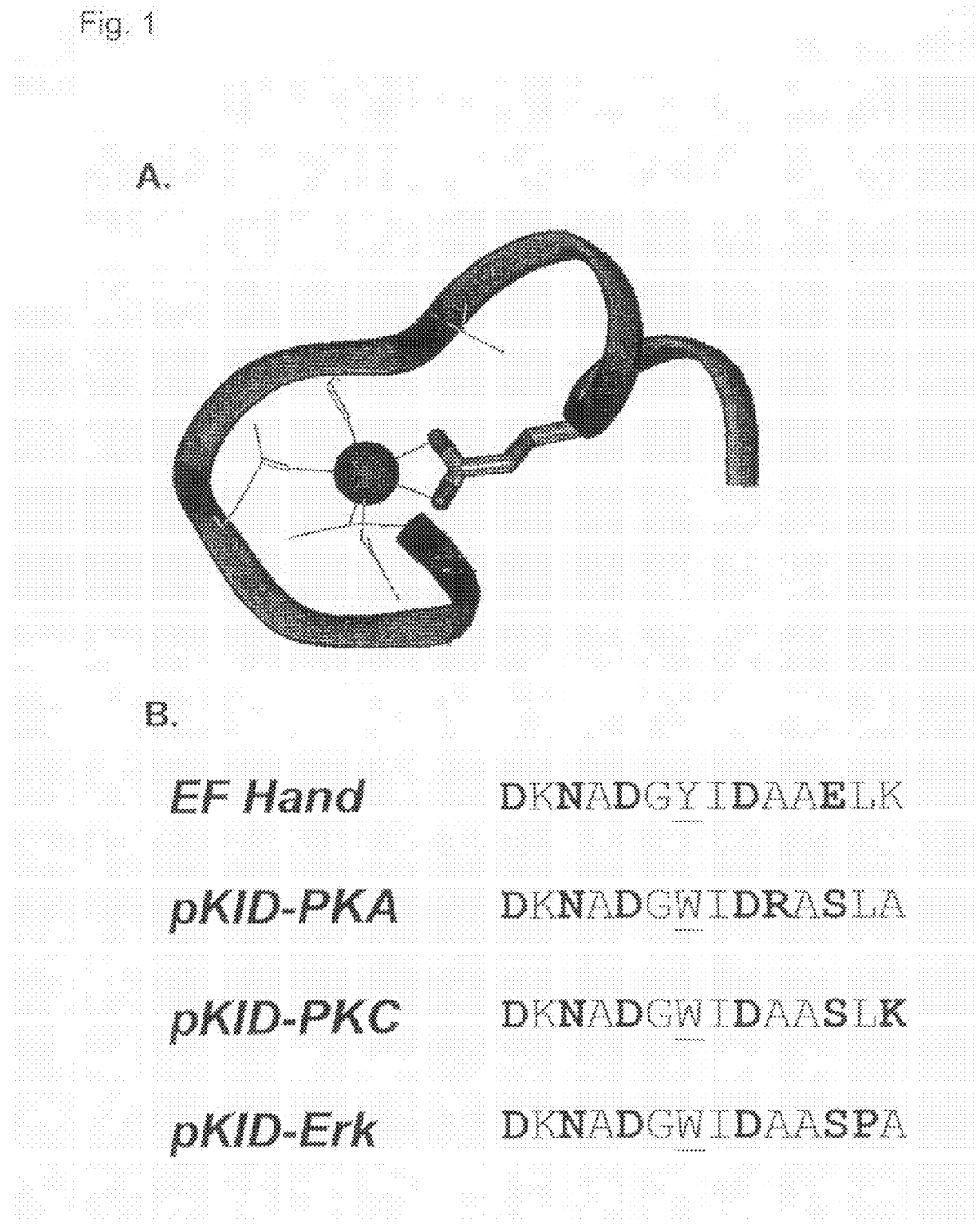
FIG. 1. A. EF hand $Ca^{2+}$-binding loop (1cll), with Glu12 emphasized. B. EF hand consensus sequence (SEQ ID NO:7) and kinase-inducible domain peptide sequences (SEQ ID NOs: 1, 3, and 5). Side changes of residues in bold text contact metal. Tyrosine or tryptophan (underlined) contacts metal via the main chain carbonyl.

A series of kinase-inducible domain (pKID) peptides were synthesized which comprised an EF hand consensus sequence, a tryptophan at residue 7 to sensitize lanthanide emission, and the recognition sequence of a kinase important in intracellular signaling (see FIG. 1). As initial targets, Applicants synthesized peptides containing the minimal recognition sequences, which include basic or helix-breaking residues that could potentially disrupt lanthanide binding and include residues N-terminal and C-terminal to the target serine, provide a significant test of the generality of the design.

Phosphorylation of pKID-PKA by Protein Kinase A

Figure 3:
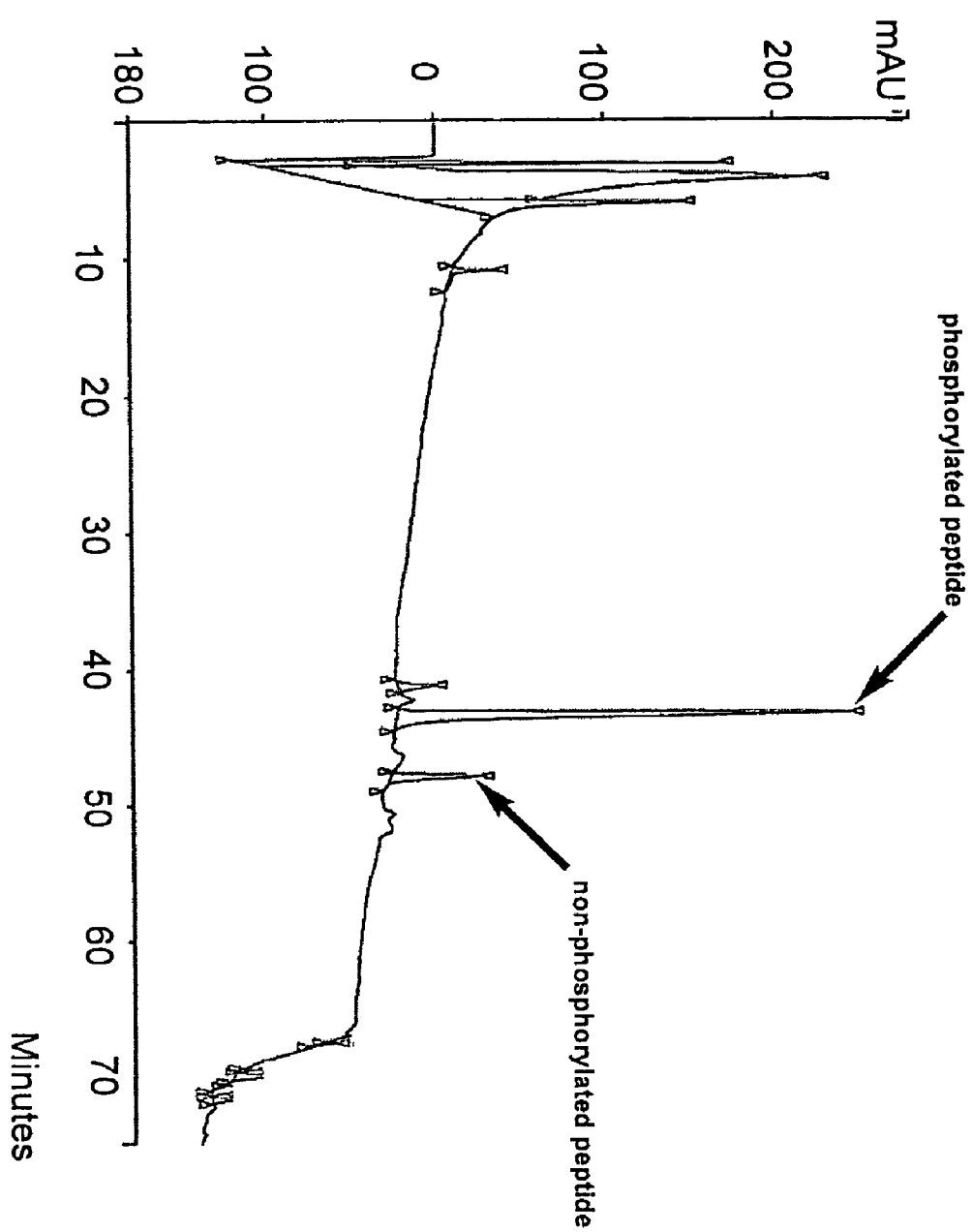
FIG. 3. Analytical HPLC chromatogram (UV detection at 215 nm) of the PKA reaction mixture after 18 hrs incubation, using a linear gradient of 0-40% buffer B (80% MeCN, 20% $H_2O$, 0.05% TFA) in buffer A (98% $H_2O$, 2% MeCN, 0.06% TFA) over 60 mins on a Rainin Microsorb MV C18 column (4.6×250 mm, 100 Å pore). Peaks were identified by ESI-MS and by coinjection with the purified non-phosphorylated and phosphorylated pKID-PKA peptides.

Protein Kinase A (PKA) and PKA reaction buffer were purchased from New England Biolabs. PKA reaction mixtures were prepared to a final volume of 25 μL as follows: stock solutions were mixed to yield final concentrations of 2.4 mM ATP (6 μL of 10 mM ATP (Alexis Biochemicals)), 1.2× PKA buffer (3 μL of 10× buffer), and 240 μM non-phosphorylated pKID-PKA (16 μL of a 370 μM stock solution). After incubation at 30° C. for 5 min, 1.5 μL of PKA enzyme solution (3.75 units) was added to start the reaction. After 12-22 hours, the reaction mixture was analyzed by HPLC, fluorescence, and ESI-MS (see FIG. 3 and Table 2).

Figure 4:
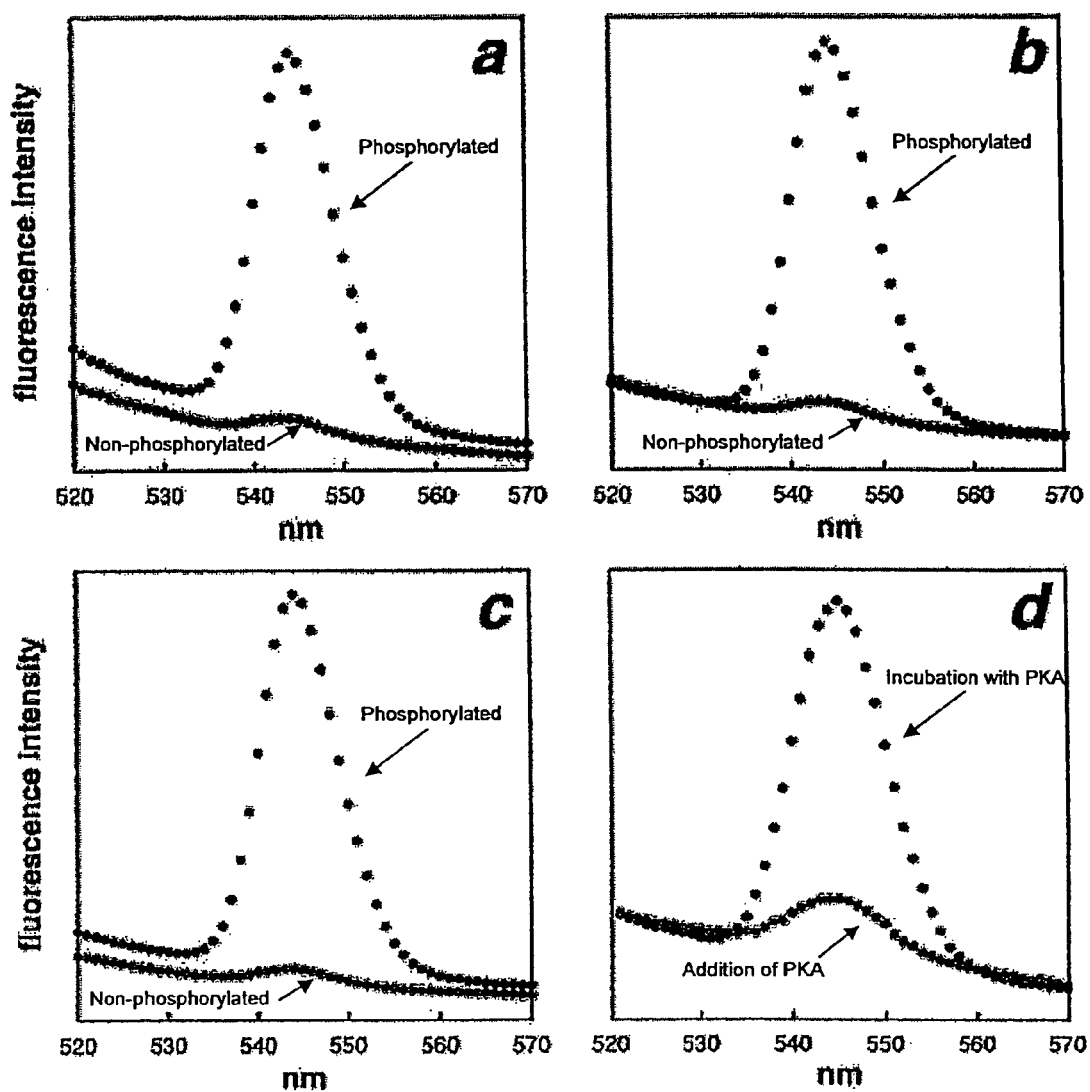
FIG. 4. (a, b, c): Fluorescence spectra of 10 μM (a) pKID-PKA, (b) pKID-PKC, or (c) pKID-Erk when non-phosphorylated or phosphorylated in the presence of 20 μM $Tb^{3+}$. Experiments were conducted in buffer containing 5 mM HEPES (pH 7.8) and 100 mM NaCl. (d): Detection of protein kinase A (PKA) activity using pKID-PKA. Fluorescence spectra were collected immediately after addition of PKA and after incubation with PKA.

The kinase reaction mixtures (25 μL, 240 μM peptide) were diluted with 1 mL of a solution containing 5 mM HEPES buffer (pH 7.8) 100 mM NaCl and 50 μM $Tb^{3+}$ and analyzed by fluorescence (see FIG. 4d) as described previously, except that 10 nm slit widths were used.

TABLE 2

Characterization data of the peaks observed in the HPLC chromatogram of the phosphorylation of pKID-PKA by protein kinase A.

| Retention time, min | Peptide | Calculated mass | Observed mass $[M - H]^-$ |
|---|---|---|---|
| 43.2 | phosphorylated pKID-PKA | 1651.8 | 1650.8 |
| 47.8 | non-phosphorylated pKID-PKA | 1571.8 | 1570.8 |

Results

Fluorescence emission spectra revealed that the non-phosphorylated peptides bound $Tb^{3+}$ poorly (see FIG. 4), displaying very weak terbium luminescence, consistent with the critical role of the Glu12 in metal binding. In contrast, all phosphorylated peptides displayed strong fluorescence emission in the presence of $Tb^{3+}$, indicating the formation of a phosphopeptide-metal complex. Notably, the fluorescence change upon phosphorylation by protein kinase A (see FIG. 4d) was similar to that observed in non-expressible kinase sensors, and was significantly greater than that of any expressible kinase sensor (for a recent review, see [30]; for leading references see [31-45]).

Example 2

Phosphorylation of pKID-PKA by Protein Kinase A in HeLa Nuclear Extract

Figure 5:
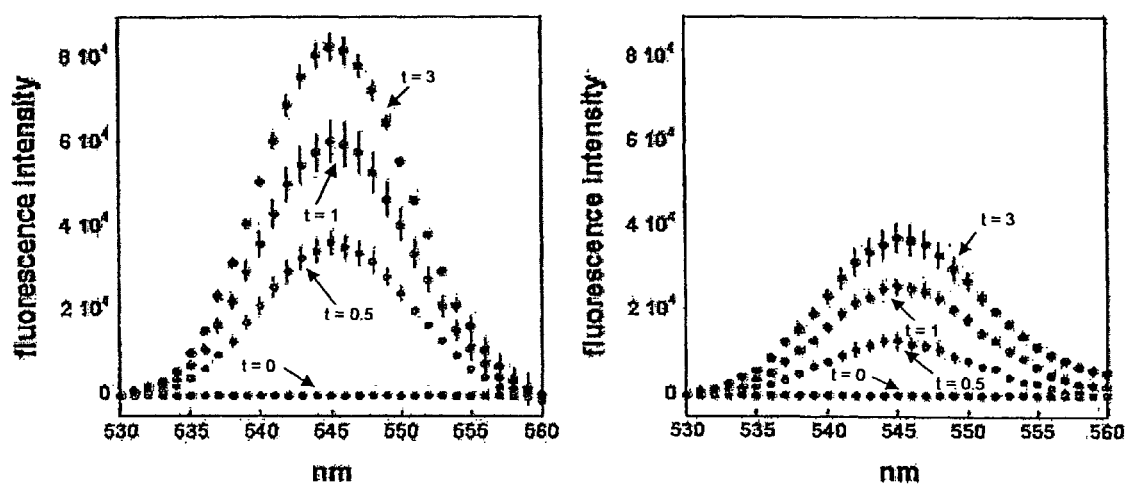
FIG. 5. Left: Fluorescence spectra of crude mixtures including pKID-PKA indicating phosphorylation of pKID-PKA by protein kinase A in HeLa nuclear extract. Fluorescence spectra are shown prior to the addition of kinase (t=0 h) and at t=0.5 h, t=1 h and t=3 h. The increase in fluorescence correlated with the extent of phosphorylation, as determined by HPLC (FIG. 6) and by fluorescence spectrum under identical conditions of chemically phosphorylated pKID-PKA. Right: Fluorescence spectra of crude mixtures of HeLa nuclear extract without added kinase. Fluorescence spectra are shown at t=0, t=0.5 h, t=1 h and t=3 h. pKID-PKA was phosphorylated by endogenous kinase present within the HeLa extracts as determined by HPLC.
Figure 6:
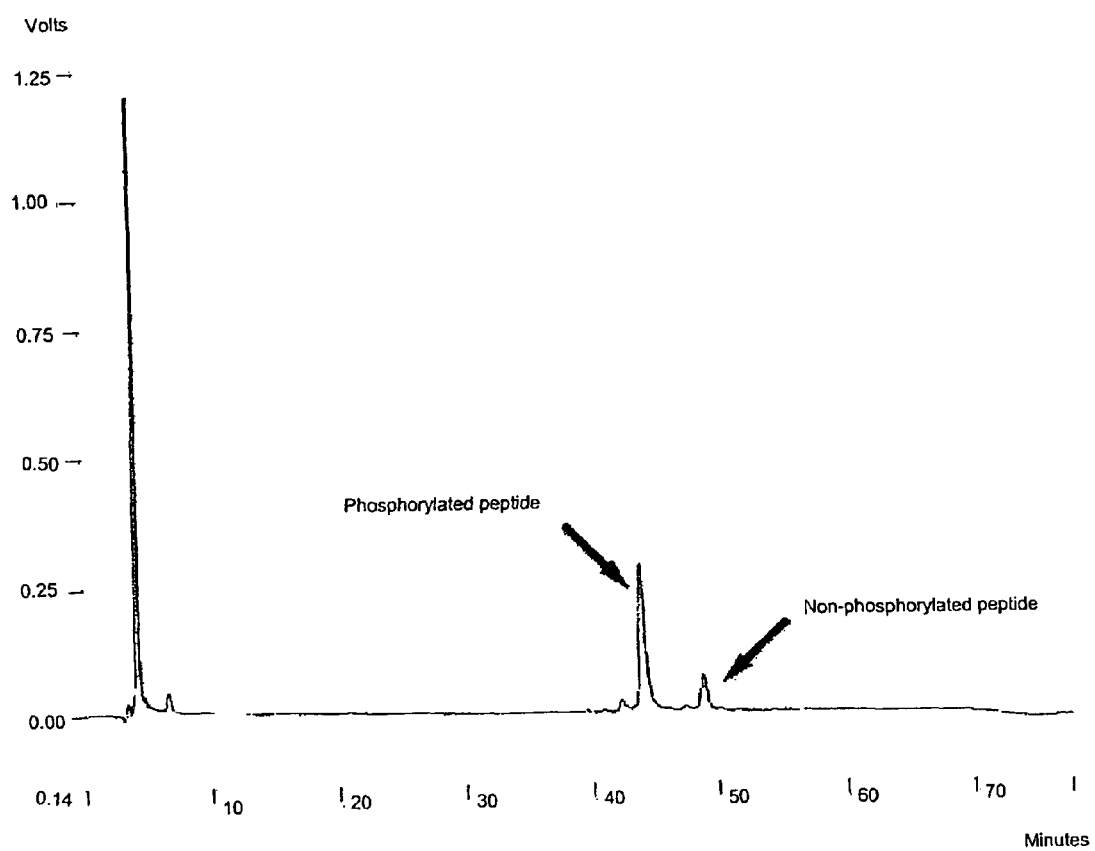
FIG. 6. Analytical HPLC chromatogram (UV detection at 215 nm) indicating phosphorylation of pKID-PKA in HeLa nuclear extract after 3 h incubation (red circles on the left panel of FIG. 5). Non-phosphorylated and phosphorylated peptides were separated using a linear gradient of 0-40% buffer B (80% MeCN, 20% $H_2O$, 0.05% TFA) in buffer A (98% $H_2O$, 2% MeCN, 0.06% TFA) over 60 mins on a Rainin Microsorb MV C18 column (4.6×250 mm, 100 Å pore). Peaks were characterized by ESI-MS. Phosphorylation proceeded at 75% conversion as measured by HPLC, consistent with the observed increase in fluorescence.

Protein Kinase A (PKA) and PKA reaction buffer were purchased from New England Biolabs. In vitro transcription grade HeLaScribe® nuclear extract was purchased from Promega (storage buffer: 40 mM Tris-HCl (pH 7.8 at 25° C.), 25% glycerol, 0.1 M KCl, 0.2 mM EDTA, 0.5 mM PMSF, 0.5 mM DTT). Reaction mixtures were prepared to a final volume of 25 µL as follows: stock solutions were mixed to yield final concentrations of 5 mM ATP (7.5 µL of 20 mM ATP (Alexis Biochemicals)), 1.2 mg/mL HeLa nuclear extract (2 µL of HeLaScribe® HeLa nuclear extract (13.8 mg/mL)), 1.2×PKA buffer (3 µL of 10× buffer), and 500 µM non-phosphorylated pKID-PKA. After incubation at 30° C. for 5 min, 3 µL of PKA enzyme solution (7.6 units) was added to start the reaction. After specified reaction times, the reaction mixture was analyzed by fluorescence (see FIG. 5, left). The kinase reaction mixtures (25 µL, 500 µM peptide) were diluted with 200 µL of a solution containing 5 mM HEPES buffer (pH 7.8), 100 mM NaCl and 100 µM $Tb^{3+}$ and analyzed by fluorescence as described previously, using 10 nm slit widths. The fluorescence spectra were background corrected. Each time point represents an independent experiment. Data represent the average of three independent trials for each time point. Error bars indicate standard error.

Phosphorylation of pKID-PKA in HeLa nuclear extract in the absence of added kinase was also examined. Reaction mixtures were prepared as described previously to a final volume of 25 µL, but protein kinase A was not added. After addition of ATP and incubation for the indicated times, the reaction mixtures (25 µL, 500 µM peptide) were diluted with 200 µL of a solution containing 5 nM HEPES buffer (pH 7.8), 100 mM NaCl and 100 µM $Tb^{3+}$ and analyzed by fluorescence as described previously. pKID-PKA was phosphorylated by endogenous kinase present within the HeLa extracts to approximately 10% conversion as determined by fluorescence and HPLC (see FIG. 5, right).

Example 3

Specific Phosphorylation of pKID-PKA by Protein Kinase A (PKA)

Figure 7:
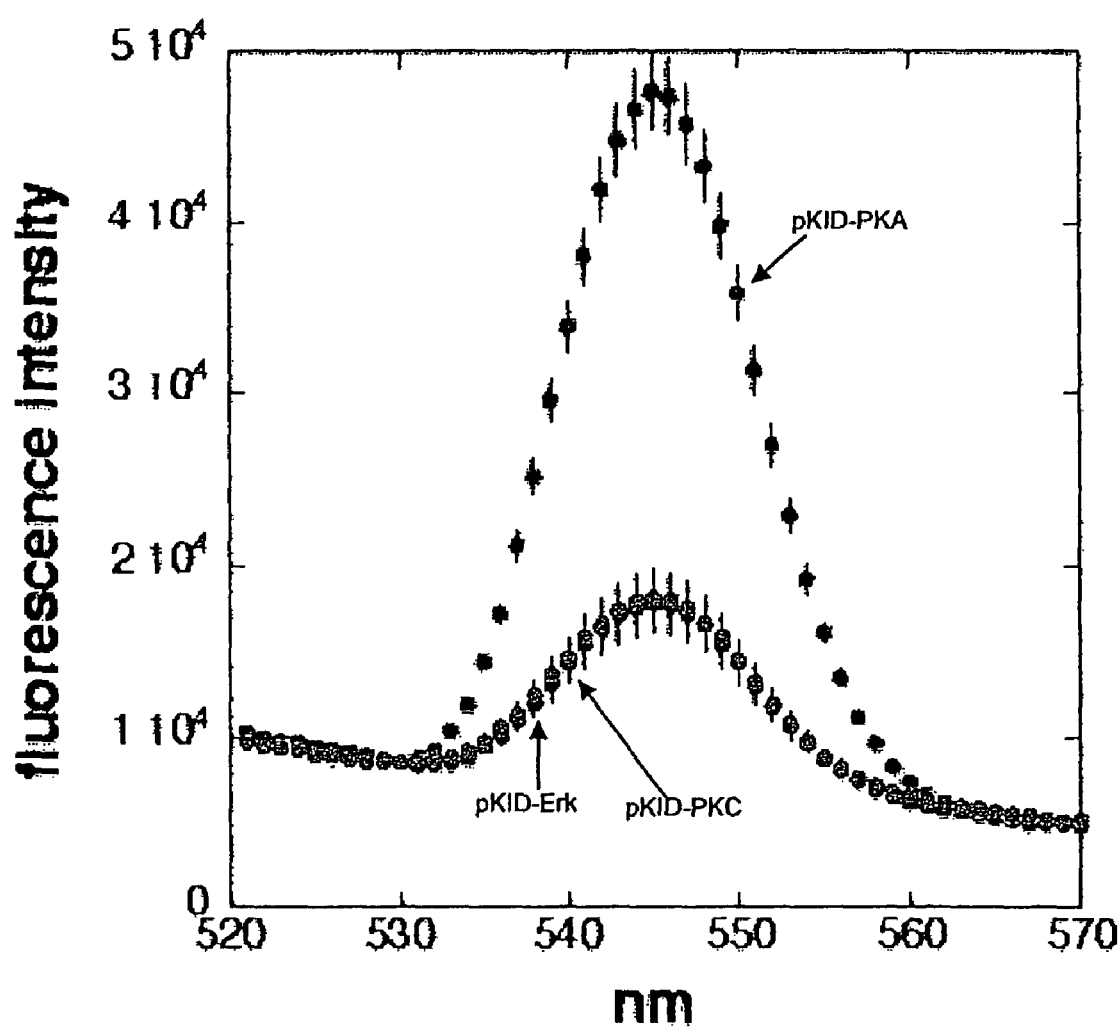
FIG. 7. Fluorescence spectra of reaction mixtures, indicating the effect of protein kinase A (PKA) on pKID-PKA, pKID-Erk, and pKID-PKC under identical conditions. pKID-PKA shows a fluorescence increase on phosphorylation with PKA corresponding to >95% conversion as determined by HPLC (FIG. 8), while pKID-Erk and pKID-PKC were not phosphorylated by PKA, as determined by HPLC (FIGS. 9 and 10, respectively).
Figure 8:
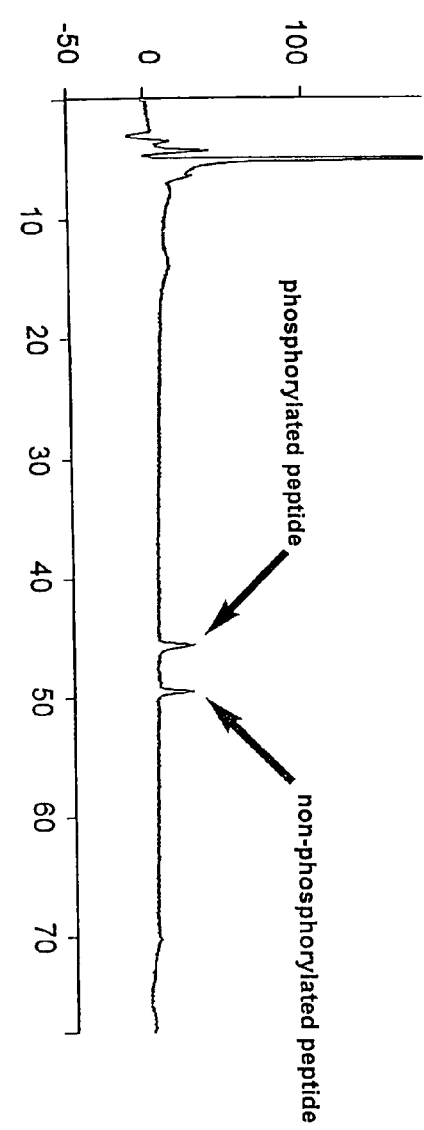
FIG. 8. Analytical HPLC chromatograms (UV detection at 215 nm) of (a) co-injection of phosphorylated and non-phosphorylated pKID-PKA and (b) pKID-PKA after incubation with protein kinase A (PKA) for 12 hours. pKID-PKA showed >95% conversion to the phosphorylated peptide when incubated with PKA. Non-phosphorylated and phosphorylated peptides were separated using a linear gradient of 0-40% buffer B (80% MeCN, 20% $H_2O$, 0.05% TFA) in buffer A (98% $H_2O$, 2% MeCN, 0.06% TFA) over 60 mins on a Rainin Microsorb MV C18 column (4.6×250 mm, 100 Å pore). Individual peaks were characterized by ESI-MS to confirm peptide identity.
Figure 8:
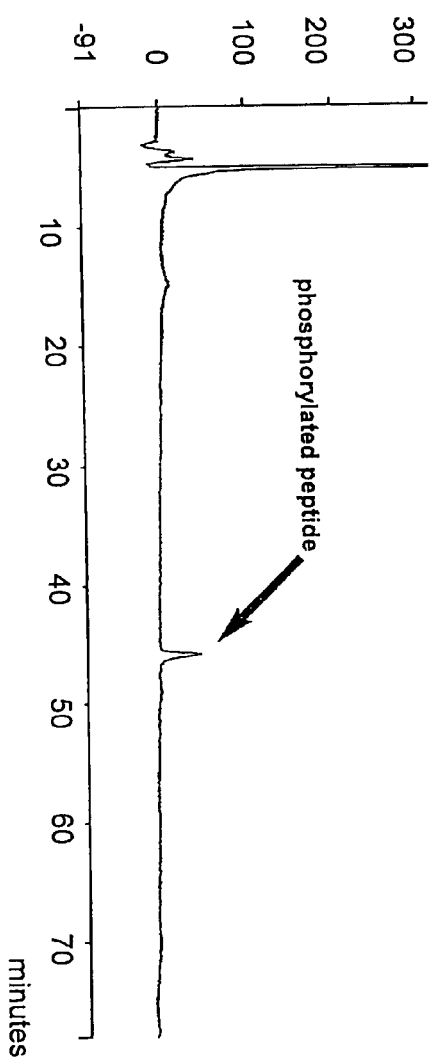
Figure 9:
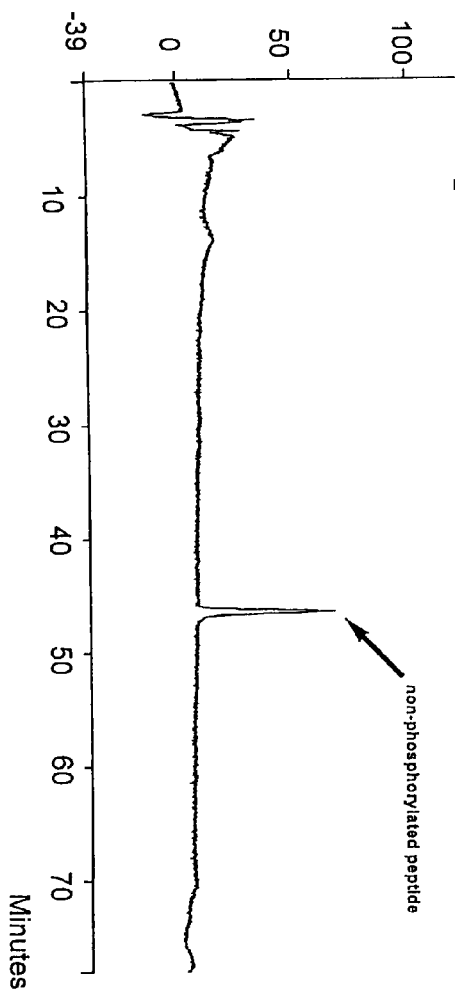
FIG. 9. Analytical HPLC chromatograms (UV detection at 215 nm) of (a) co-injection of phosphorylated and non-phosphorylated pKID-Erk and (b) pKID-Erk after incubation with protein kinase A (PKA) for 12 hours. pKID-Erk showed no evidence of phosphorylation when incubated with PKA. Non-phosphorylated and phosphorylated peptides were separated using a linear gradient of 0-40% buffer B (80% MeCN, 20% $H_2O$, 0.05% TFA) in buffer A (98% $H_2O$, 2% MeCN, 0.06% TFA) over 60 mins on a Rainin Microsorb MV C18 column (4.6×250 mm, 100 Å pore). Individual peaks were characterized by ESI-MS to confirm peptide identity.
Figure 9:
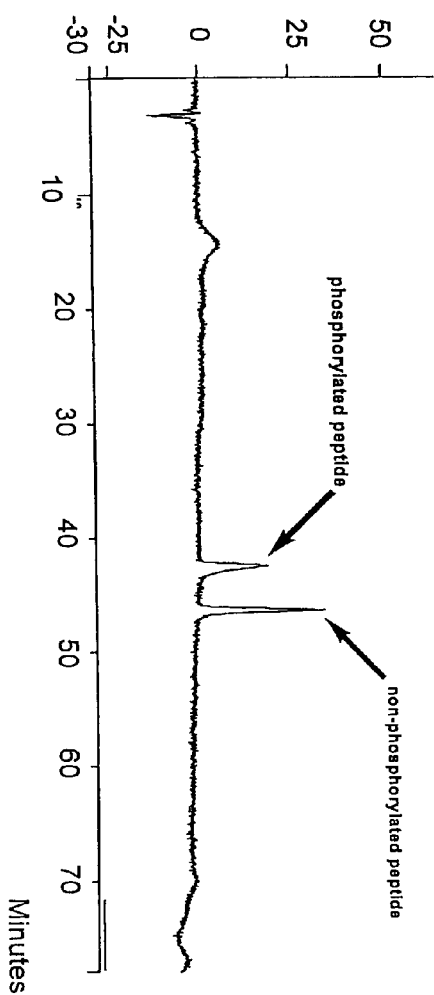
Figure 10:
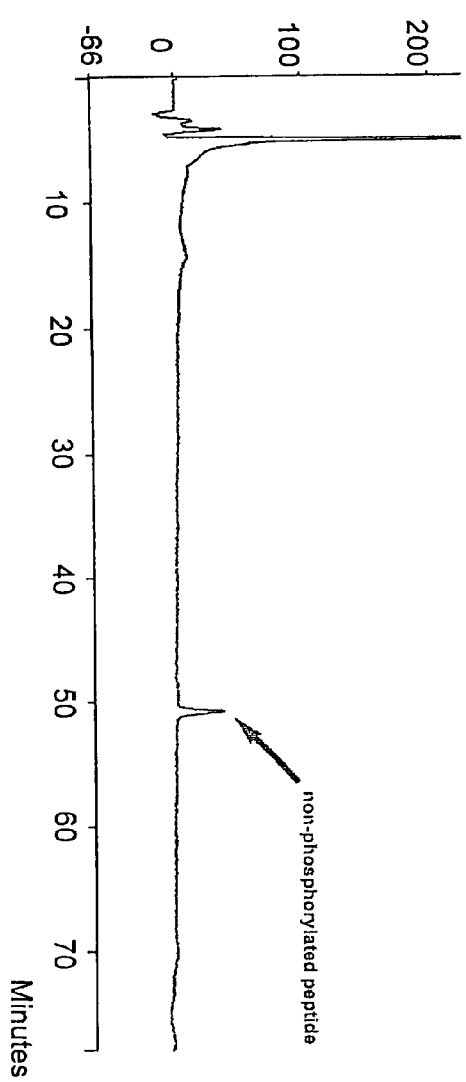
FIG. 10. Analytical HPLC chromatograms (UV detection at 215 nm) of (a) co-injection of phosphorylated and non-phosphorylated pKID-PKC and (b) pKID-PKC after incubation with protein kinase A (PKA) for 12 hours. pKID-PKC showed no evidence of phosphorylation when incubated with PKA. Non-phosphorylated and phosphorylated peptides were separated using a linear gradient of 0-40% buffer B (80% MeCN, 20% $H_2O$, 0.05% TFA) in buffer A (98% $H_2O$, 2% MeCN, 0.06% TFA) over 60 mins on a Rainin Microsorb MV C18 column (4.6×250 mm, 100 Å pore). Individual peaks were characterized by ESI-MS to confirm peptide identity.
Figure 10:
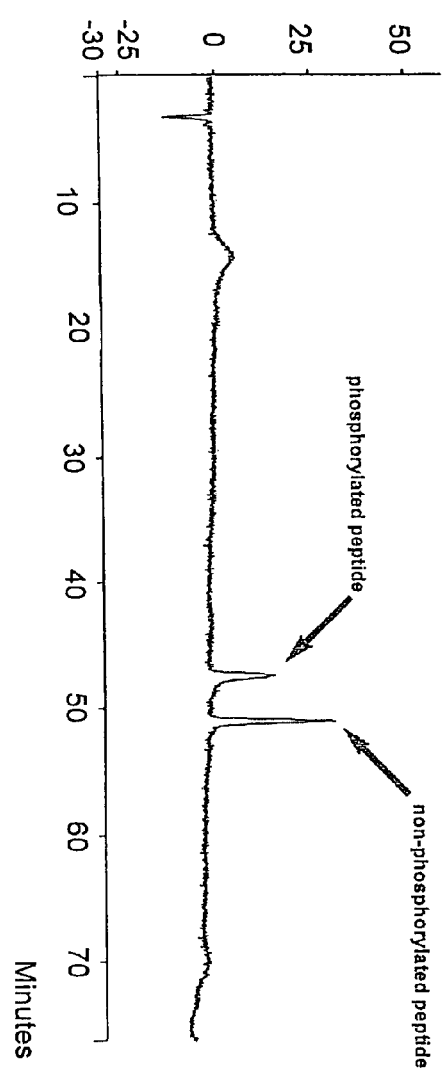

Kinase specificity for protein kinase-inducible domain peptides was examined by incubation of protein kinase A with pKID-PKA, pKID-PKC and pKID-Erk. Experiments were conducted with 2.4 mM ATP (3 µL of freshly prepared 20 mM ATP), PKA buffer (3 µL of 10× buffer), and peptide (200 µM) with water in 25 µL final reaction volume. After incubation at 35° C. for 5 min, PKA enzyme solution (1 µL, 2.5 units) was added to start the reaction. After 12-14 hrs at 35° C., the reaction mixture was analyzed by fluorescence, HPLC and ESI-MS. The kinase reaction mixtures were analyzed by fluorescence by diluting the reaction mixture with 1 mL of a solution containing 5 mM HEPES buffer (pH 7.8), 100 mM NaCl, and 50 µM $Tb^{3+}$, and the resulting solution analyzed by fluorescence. Fluorescence experiments were conducted with 10 nm slit widths and a 495 nm highpass filter on the emission monochromator. Fluorescence data (FIG. 7) represent the average of four independent trials. Error bars indicate standard error. The solutions used for the fluorescence analysis were analyzed by HPLC to quantify the extent of peptide phosphorylation. pKID-PKA was enzymatically phosphorylated to >95% conversion in 12 hrs by PKA (FIG. 8), while under identical conditions pKID-Erk (FIG. 9) and pKID-PKC (FIG. 10) showed no evidence of phosphorylation. Experiments with different peptides were conducted in parallel to assure that the enzyme activity was comparable for enzymatic reactions with different peptides.

Example 4

Dissociation Constant Determination

Figure 11:
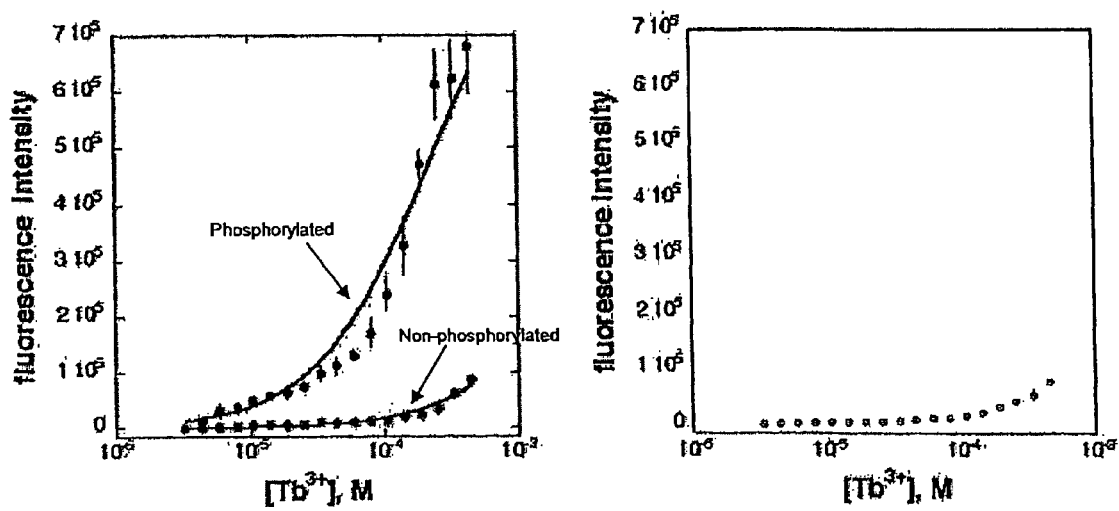
FIG. 11. Left: Titration of 10 μM non-phosphorylated pKID-PKA and phosphorylated pKID-PKA with $Tb^{3+}$. Right: Fluorescence due to $Tb^{3+}$ in the absence of peptide.
Figure 12:
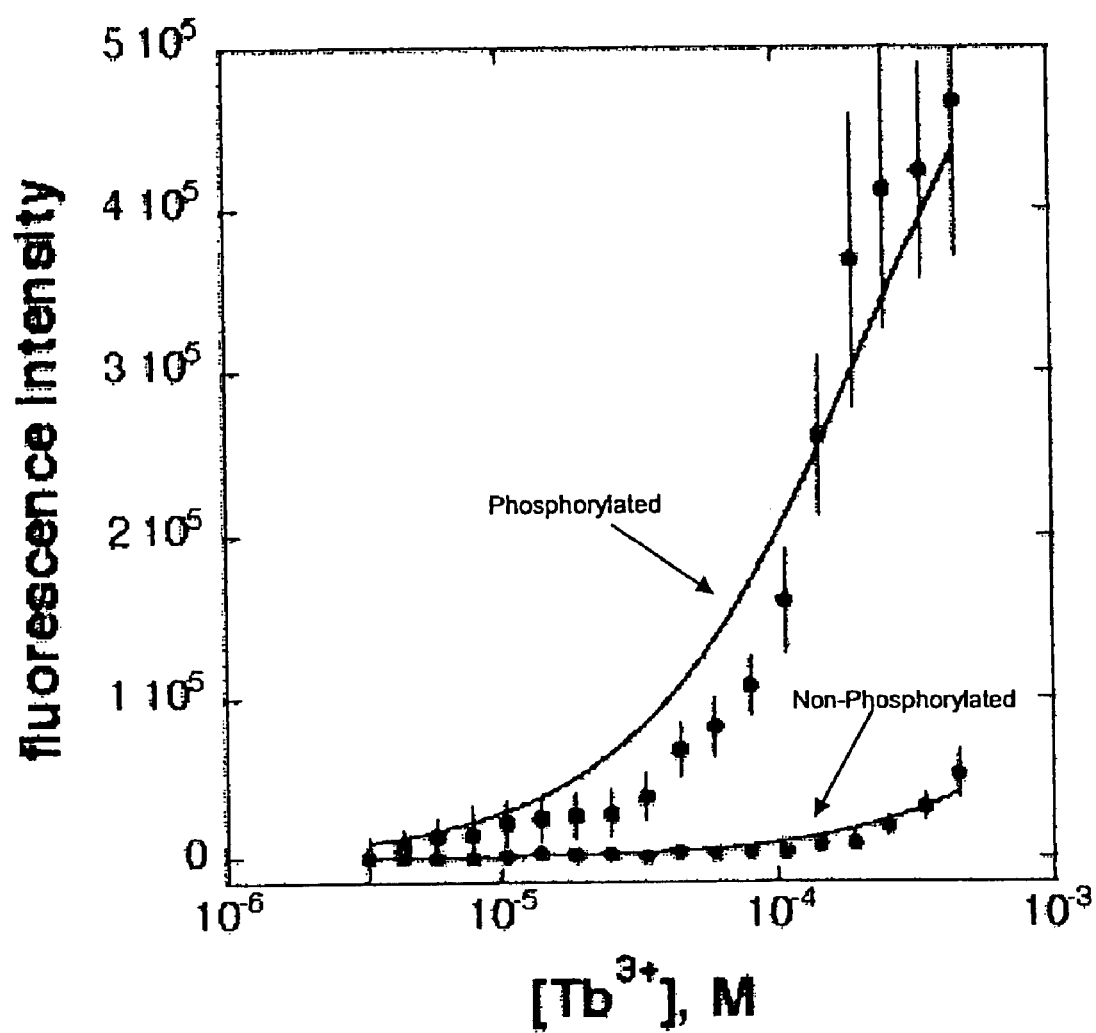
FIG. 12. Titration of 10 μM non-phosphorylated pKID-PKC and phosphorylated pKID-PKC with $Tb^{3+}$.
Figure 13:
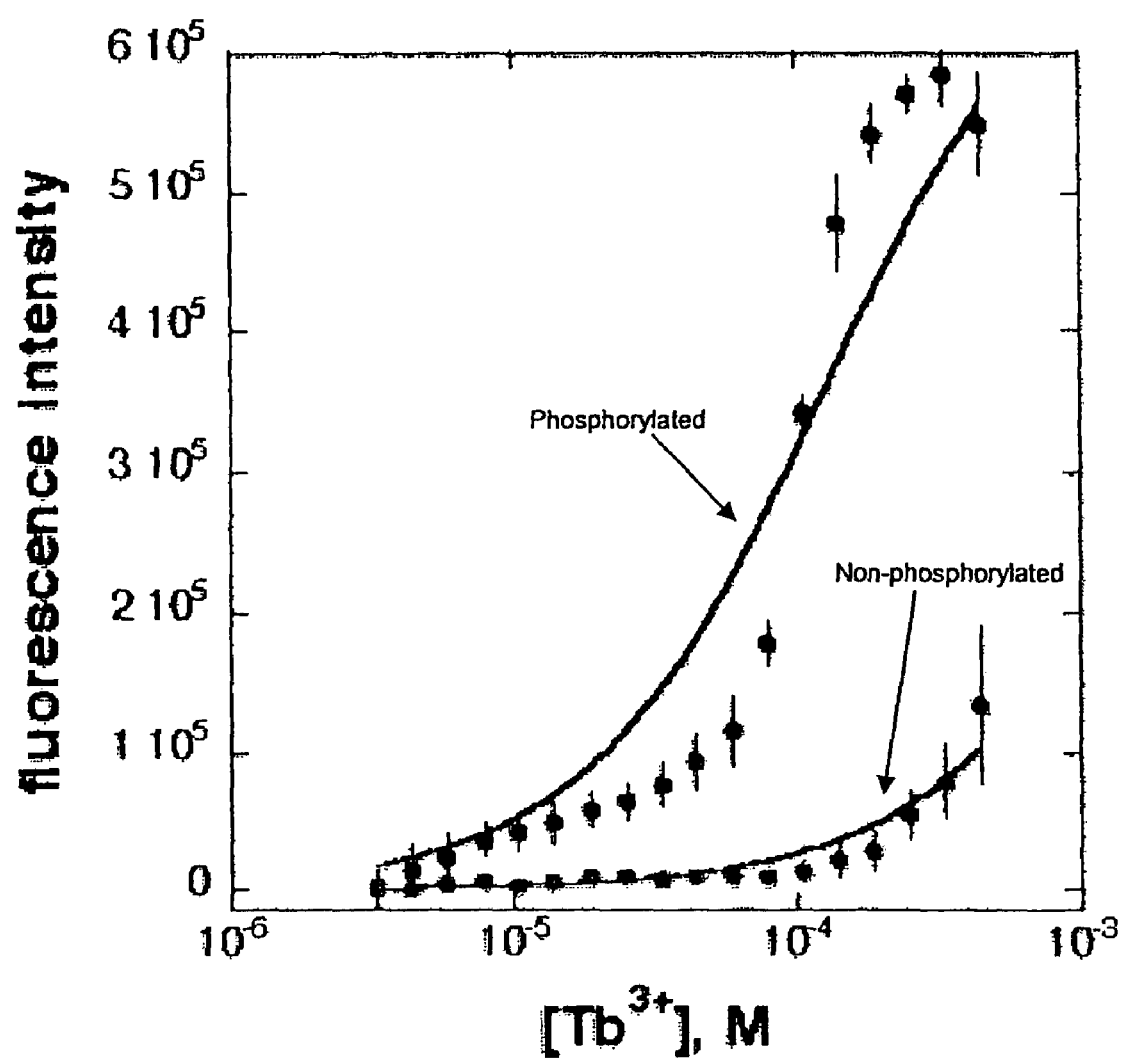
FIG. 13. Titration of 10 μM non-phosphorylated pKID-Erk and phosphorylated pKID-Erk with $Tb^{3+}$.

To determine dissociation constants for $Tb^{3+}$-peptide complexes, titrations were conducted in solutions of 5 mM HEPES (pH 7.8) and 100 mM NaCl, with 10 nm emission and excitation slit widths. All fluorescence experiments were conducted using a 495 nm highpass filter (model 495FG03-25 AM-53074; Andover Corporation, Andover, N.H.) on the emission monochromator. All $TbCl_3$ solutions were standardized by titration with a standard solution of EDTA (1 mM) in the presence of xylenol orange indicator (10 µM) and sodium acetate buffer (pH 6.0, 10 mM). 500 µL of the 1 mM $Tb^{3+}$ stock solution was diluted to 1 mL to make a 0.5 mM solution and EDTA (1 mM) was added (approximately 500 µL) until the end point was reached (see FIGS. 11-13). The solutions were prepared as serial dilutions of $Tb^{3+}$, from 3.3 µM to 450 µM $Tb^{3+}$, and the fluorescence emission scan of each solution was acquired. Data points at the emission maximum of 544 nm were plotted against $Tb^{3+}$ concentration to calculate the final $K_d$. Data points indicate the average of at least three independent titrations. Error bars indicate standard error. The data were fit to equation (1) using a non-linear least squares fitting algorithm (KaleidaGraph version 3.6, Synergy Software), where Q=fluorescence, $Q_o$=fluorescence of the apo-peptide, $Q_c$=fluorescence of peptide-metal complex, $M_t$=total metal concentration, $K_d$=dissociation constant and $P_t$=total peptide concentration (10 µM). Dissociation constants in the presence of 2 mM $Mg^{2+}$ or 100 µM $Ca^{2+}$ were measured for pKID-PKA peptides to study the effect of these metals on $Tb^{3+}$-peptide complex formation.

$$Q = Q_o + (Q_c - Q_o) \frac{\left[(M_t + K_d + P_t) - \sqrt{(M_t + P_t + K_d)^2 - 4(P_t M_t)}\right]}{2 P_t} \quad (1)$$

See Table 3 for dissociation constants for peptide-$Tb^{3+}$ complexes in aqueous solutions of 5 mM HEPES (pH 7.8) and 100 mM NaCl (pS indicates phosphoserine).

TABLE 3

| Peptide | Sequence | $K_d$, μM | Standard Error (±) |
|---|---|---|---|
| non-phosphorylated pKID-PKA | Ac-DKNADGWIDRASLA-NH$_2$ (SEQ ID NO:1) | >5000$^a$ | n.a. |
| non-phosphorylated pKID-PKA + 2 mM Mg$^{2+}$ | | >5000$^a$ | n.a. |
| phosphorylated pKID-PKA | Ac-DKNADGWIDRApSLA-NH$_2$ (SEQ ID NO:2) | 220 | 16 |
| phosphorylated pKID-PKA + 100 uM Ca$^{2+}$ | | 228 | 11 |
| phosphorylated pKID-PKA + 2 mM Mg$^{2+}$ | | 174 | 14 |
| non-phosphorylated pKID-PKC | Ac-DKNADGWIDAASLK-NH$_2$ (SEQ ID NO:3) | >6000$^a$ | n.a. |
| phosphorylated pKID-PKC | Ac-DKNADGWIDAApSLK-NH$_2$ (SEQ ID NO:4) | 216 | 20 |
| non-phosphorylated pKID-Erk | Ac-DKNADGWIDAASPA-NH$_2$ (SEQ ID NO:5) | >3000$^a$ | n.a. |
| phosphorylated pKID-Erk | Ac-DKNADGWIDAApSPA-NH$_2$ (SEQ ID NO:6) | 124 | 16 |

$^a$Non-phosphorylated peptides bound Tb$^{3+}$ very poorly and did not display evidence of saturation binding, precluding accurate determination of dissociation constants for these peptide-Tb$^{3+}$ complexes.

Dissociation constants of the non-phosphorylated peptides were calculated by defining the maximum fluorescence of the non-phosphorylated peptide-Tb$^{3+}$ complex as equal to the maximum fluorescence of the phosphorylated peptide-Tb$^{3+}$ complex: $Q_c$ (non-phosphorylated peptide)=$Q_c$ (phosphorylated peptide), with $Q_c$=the calculated fluorescence of the fully bonded phosphopeptide-Tb$^{3+}$ complex. Although the assumption of similar maximum fluorescence intensities of the Tb$^{3+}$ complexes of the non-phosphorylated and phosphorylated peptides may not be valid, it provides a measure of relative Tb$^{3+}$ fluorescence of the phosphorylated and non-phosphorylated peptides.

All peptides displayed nearly complete dependence on phosphorylation for fluorescence.

Example 5

Ho$^{3+}$ Competition Experiments

Competition experiments were used to confirm site-specific lanthanide binding and to address whether pKID peptides are a general phosphorylation-dependent lanthanide-binding motif. In order to determine whether Tb$^{3+}$ binding is site-specific, competition experiments were performed with Ho$^{3+}$. Ho$^{3+}$ solutions were prepared from hydrates of the chloride salts in ultrapure water. The phosphorylated pKID-PKC peptide was tested for Ho$^{3+}$ binding by addition of aliquots of Ho$^{3+}$ to a solution containing 10 μM phosphorylated pKID-PKC and 10 μM Tb$^{3+}$. pKID-Tb$^{3+}$-Ho$^{3+}$ solutions were allowed to equilibrate for 2 minutes. Fluorescence experiments were conducted using a 495 nm highpass filter (model 495FG03-25 AM-53074; Andover Corporation, Andover, N.H.) on the emission monochromator and 8 nm slit widths.

Figure 14:
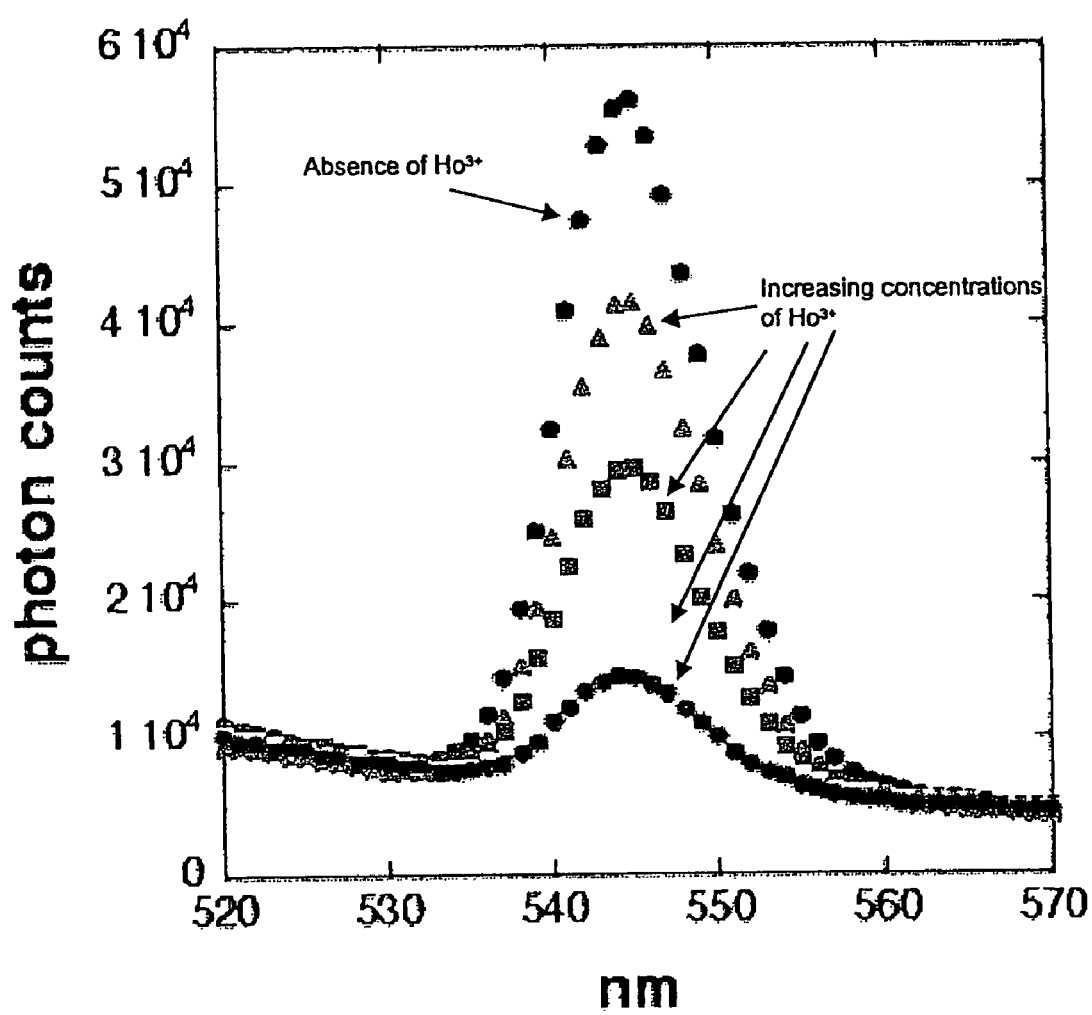
FIG. 14. Competitive reduction of $Tb^{3+}$ luminescence with $Ho^{3+}$. Fluorescence spectra of a solution of 10 μM phosphorylated pKID-PKC and 10 μM $Tb^{3+}$ in the absence of $Ho^{3+}$ and in the presence of increasing concentrations of $Ho^{3+}$.

Ho$^{3+}$ binding to the peptide is observed as a loss of Tb$^{3+}$ luminescence consistent with formation of a pKID-PKC-Ho$^{3+}$ complex, as is seen in FIG. 14.

Example 6

Tb$^{3+}$ Binding of pKID-PKA Peptides in the Presence of 2 mM Mg$^{2+}$

Figure 15:
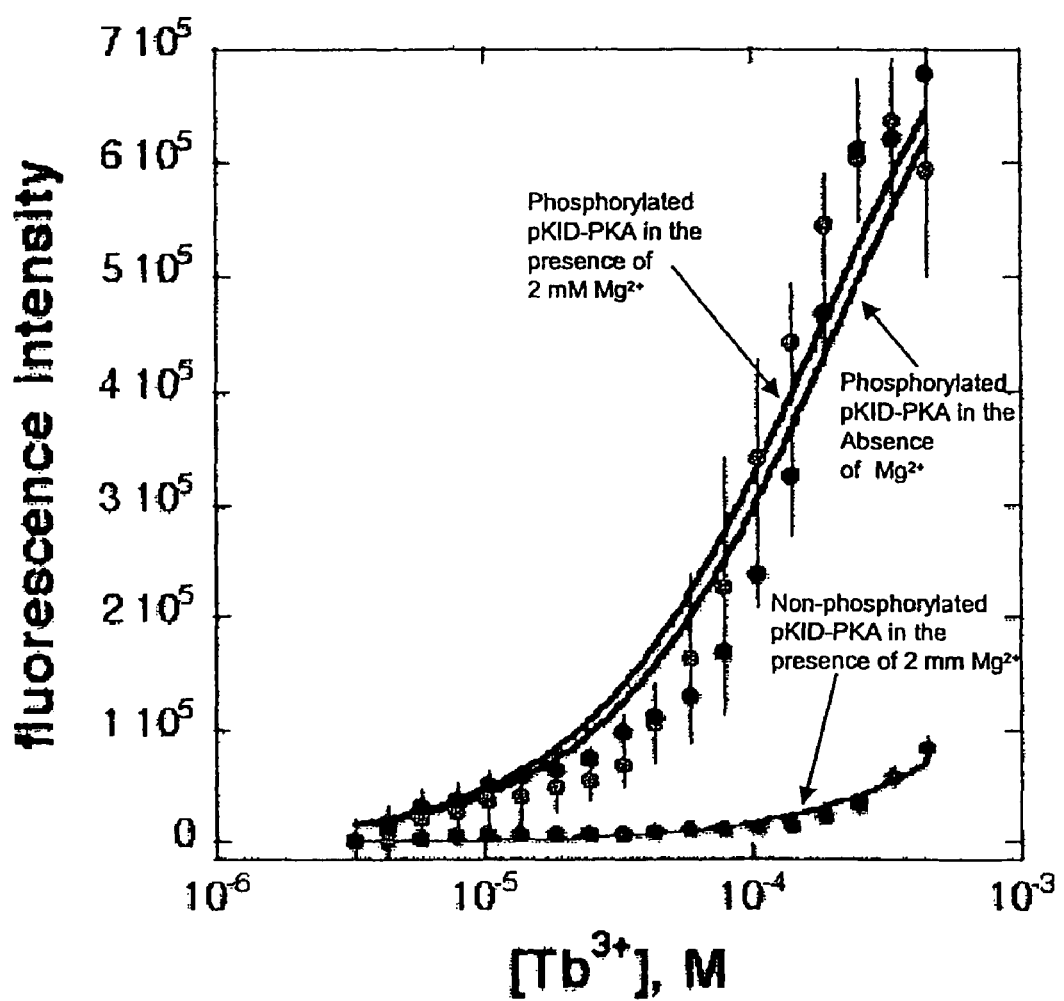
FIG. 15. $Tb^{3+}$ binding titration of 10 μM phosphorylated pKID-PKA in the presence of 2 mM $Mg^{2+}$ and in the absence of $Mg^{2+}$; and $Tb^{3+}$ binding titration of 10 μM non-phosphorylated pKID-PKA in the presence of 2 mM $Mg^{2+}$.

Tb$^{3+}$ binding experiments with the pKID-PKA peptides were conducted in the presence of 2 mM Mg$^{2+}$ to measure the effect of cellular concentrations of Mg$^{2+}$ on peptide-Tb$^{3+}$ complex stability. In the presence of 2 mM Mg$^{2+}$, the $K_d$ for phosphorylated pKID-PKA decreased slightly (1.3-fold). See FIG. 15. In contrast, Tb$^{3+}$ binding was not observed for the non-phosphorylated peptide pKID-PKA in the presence of Mg$^{2+}$. Tight peptide-Tb$^{3+}$ complex formation is dependent on phosphorylation and is not affected by 2 mM Mg$^{2+}$.

Example 7

Tb$^{3+}$ Binding of pKID-PKA Peptides in the Presence of 100 μM Ca$^{2+}$

Figure 16:
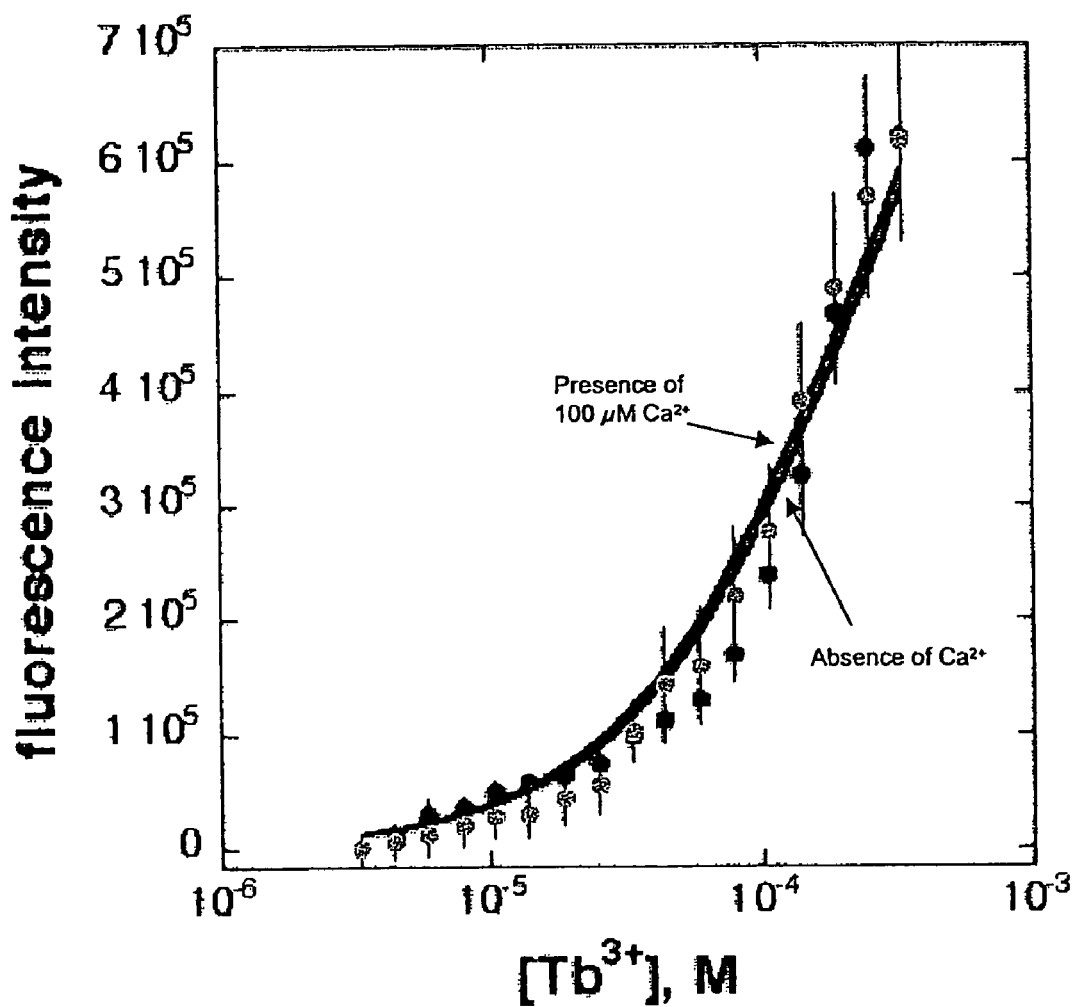
FIG. 16. $Tb^{3+}$ binding titration with 10 μM phosphorylated pKID-PKA in the absence of $Ca^{2+}$ and in the presence of 100 μM $Ca^{2+}$.

The binding of Tb$^{3+}$ to phosphorylated pKID-PKA in the presence of 100 μM Ca$^{2+}$ was examined. The fluorescence emission spectra of 10 μM phosphorylated pKID-PKA were analyzed in the absence and presence of 100 μM Ca$^{2+}$. Samples were prepared and spectra were collected as described previously, using 10 nm slit widths. The dissociation constant of the phosphopeptide-Tb$^{3+}$ complex did not significantly change in the presence of 100 μM Ca$^{2+}$ (see FIG. 16).

Example 8

Circular Dichroism of Phosphorylated pKID-PKA

Figure 17:
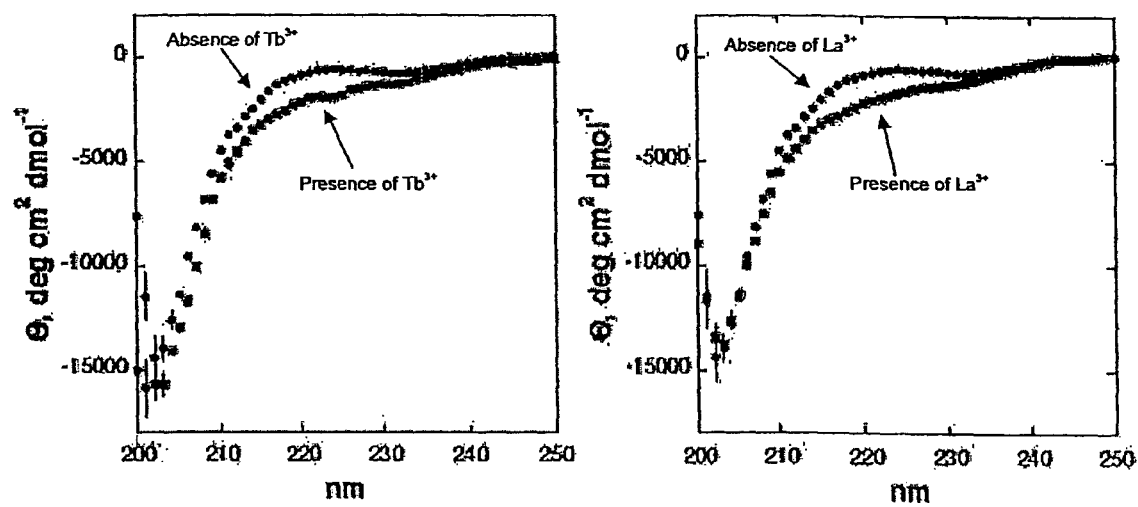
FIG. 17. Left: CD spectra of 100 μM phosphorylated pKID-PKA in the absence (circles) and presence (squares) of 500 μM $Tb^{3+}$. Right: CD spectra of 100 μM phosphorylated pKID-PKA in the absence (circles) and presence (squares) of 500 μM $La^{3+}$.

Metal Binding to phosphorylated pKID-PKA was examined by circular dichroism (CD). CD spectra were collected at 25° C. on a Jasco J-810 Spectropolarimeter in a 2 mm quartz cell (Starna) with 100 µM phosphorylated pKID-PKA in $H_2O$ with 10 mM HEPES (pH 7.8) and 10 mM NaCl in the absence and presence of 500 µM $Tb^{3+}$ or 500 µM $La^{3+}$. Data were collected every 1 nm with an averaging time of 4 s, 2 accumulations, and a 2 nm bandwidth. Error bars are shown and indicate standard error. Data represent the average of three independent trials. See FIG. 17.

Example 9

NMR Spectroscopy

Figure 18:
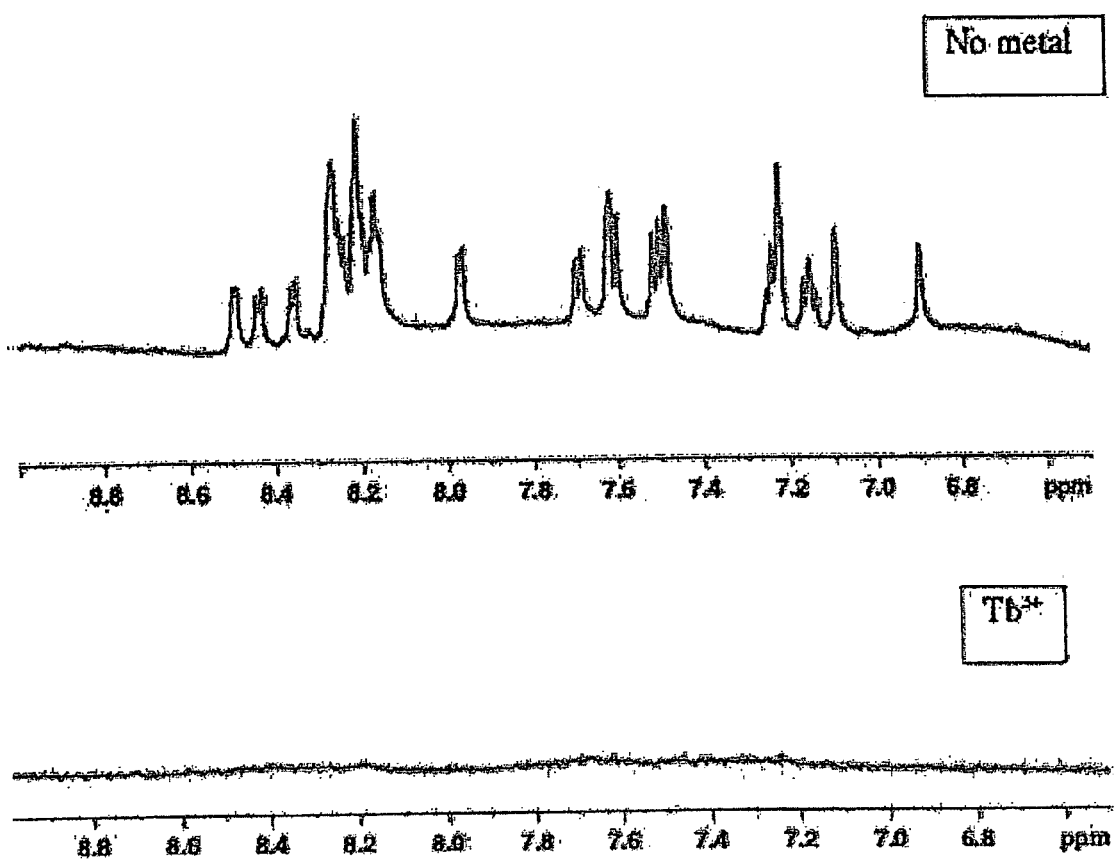
FIG. 18. 1-D NMR spectra of 1 mM phosphorylated pKID-PKC in the absence and presence of 1 mM $Tb^{3+}$. Extreme broadening of the resonances is consistent with paramagnetic shifts and relaxation due to phosphopeptide-$Tb^{3+}$ complex formation.
Figure 19:
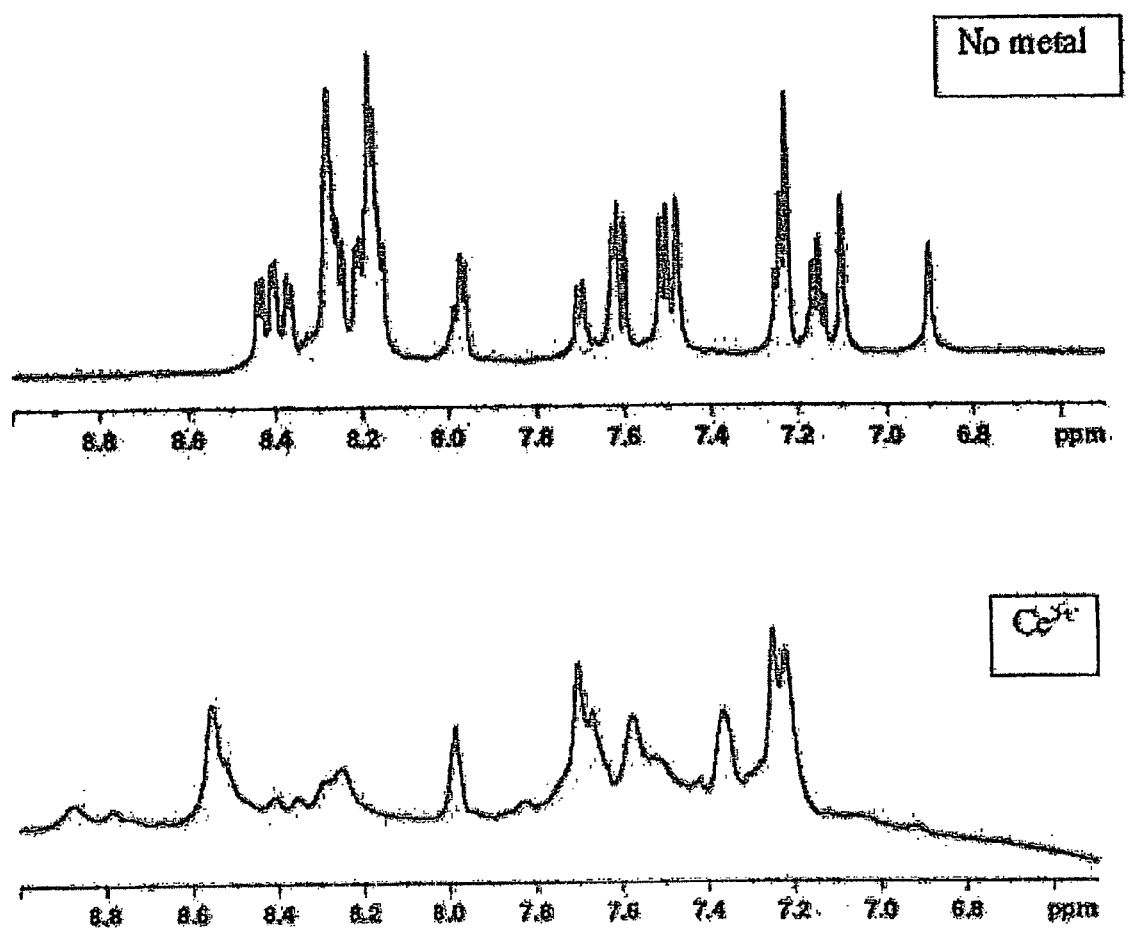
FIG. 19. 1-D NMR spectra of 1 mM phosphorylated pKID-PKC in the absence and presence of 1 mM $Ce^{3+}$. Broadening and shifting of the resonances is consistent with paramagnetic shifts and relaxation due to phosphopeptide-$Ce^{3+}$ complex formation.
Figure 20:
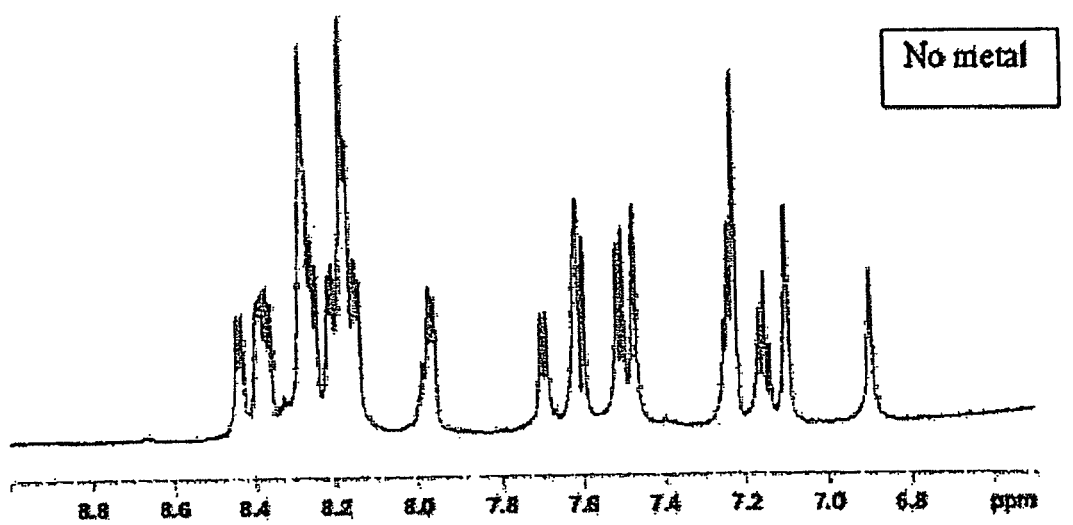
FIG. 20. 1-D NMR spectra of 1.5 mM phosphorylated pKID-PKC in the absence and presence of 1.5 mM $La^{3+}$.
Figure 20:
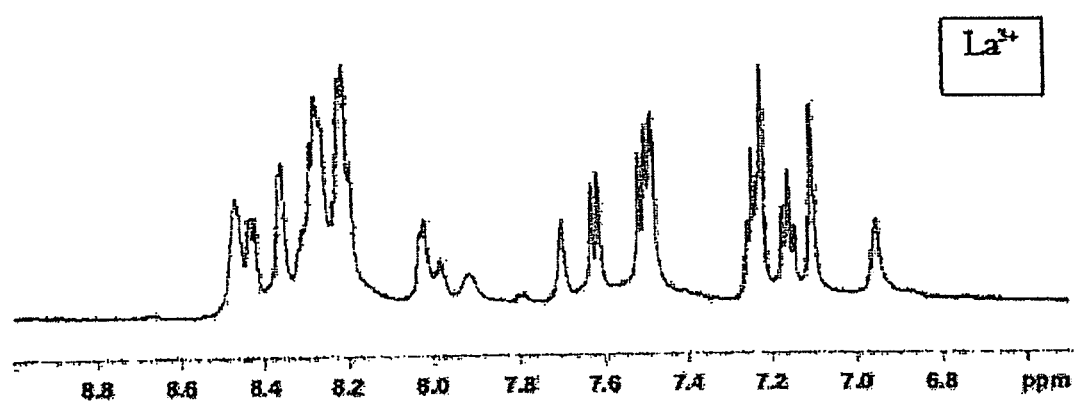
Figure 21:
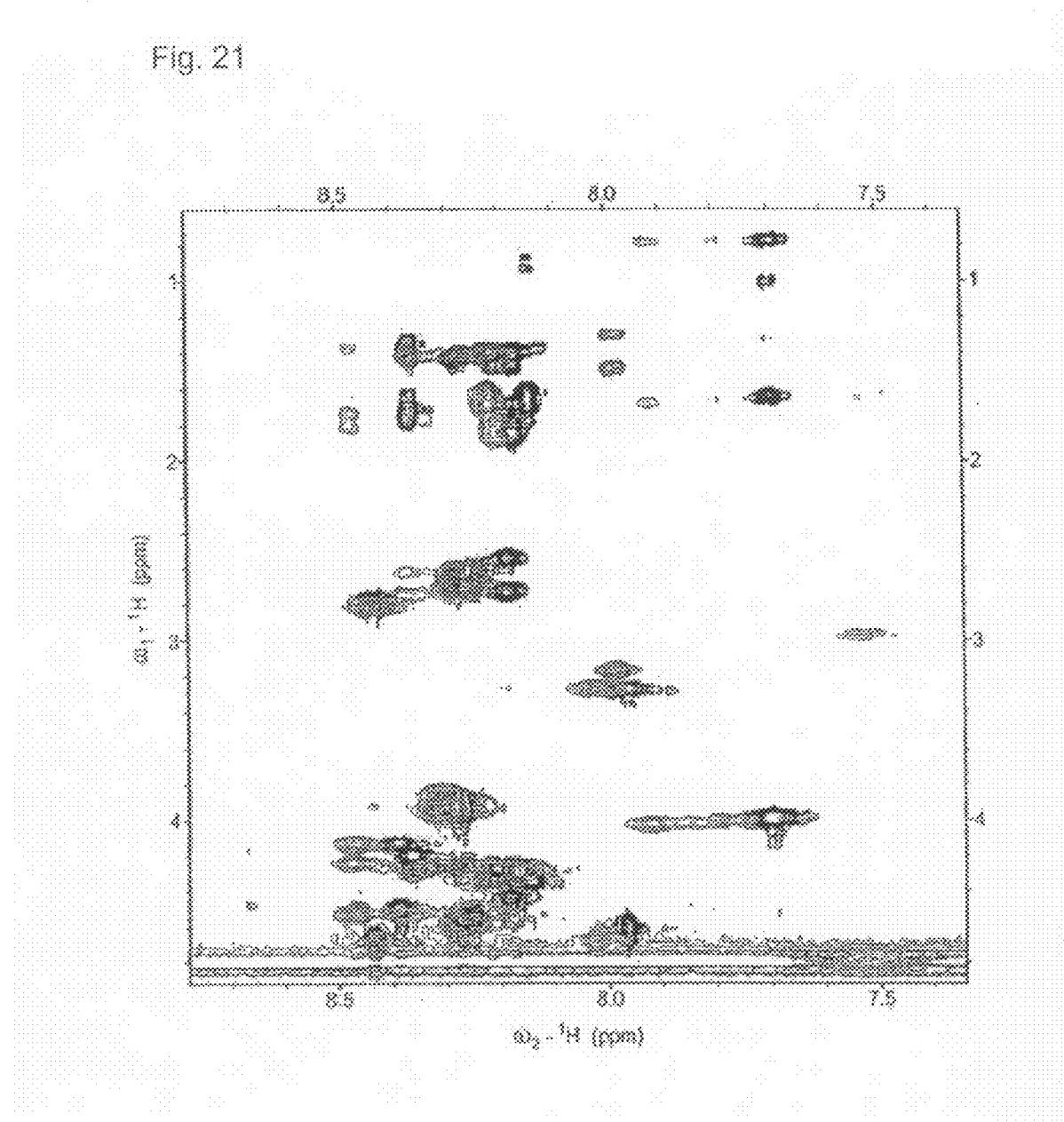
FIG. 21. TOCSY spectra of 1.5 mM phosphorylated pKID-PKC in the absence (dark contours) and presence (light contours) of 1.5 mM $La^{3+}$.

Metal binding was further characterized by NMR. NMR samples of phosphorylated pKID-PKC were prepared as 1-1.5 mM peptide solutions containing 10 mM deuterated acetate buffer (pH 6.1), 1.5 mM TSP[D4] (ICN Biomedicals), 100 mM NaCl, and 10% $D_2O$ and 90% $H_2O$ in a total volume of 400 µL. NMR experiments were conducted in the absence of metal, in the presence of two paramagnetic metals, $Tb^{3+}$ (FIG. 18) and $Ce^{3+}$ (FIG. 19), and in the presence of the diamagnetic metal $La^{3+}$ (FIG. 20) to evaluate changes due to metal-phosphopeptide complex formation. All metals were used as the metal(III) chloride salts. NMR spectra were collected on a Brüker AVC 600 MHz NMR spectrometer equipped with a triple-resonance cryoprobe. 1-D spectra and TOCSY spectra were collected with water suppression using a Watergate w5 pulse sequence with gradients (Bruker pulse programs zggpw5 and mlevgpphw5, respectively). $^1H$-$^{15}N$ HSQC experiments were conducted with Watergate water suppression (Brüker pulse program hsqcfpf3gpphwg). 1-D spectra were collected with a sweep width of 7183 Hz, 8192 data points, and a relaxation delay of 3 s. TOCSY spectra were acquired with sweep widths of 7183 Hz in $t_1$ and $t_2$, with 600×2048 complex data points, 2 scans per $t_1$ increment, and a relaxation delay of 2 s. $^1H$-$^{15}N$ HSQC experiments were conducted using the peptides with natural abundance $^{15}N$, with sweep widths of 1824 Hz in $t_1$ and 5387 Hz in $t_2$, with 80×1024 complex data points, 128-192 scans per $t_1$ increment, and a relaxation delay of 2 s (see FIG. 21).

Figure 22:
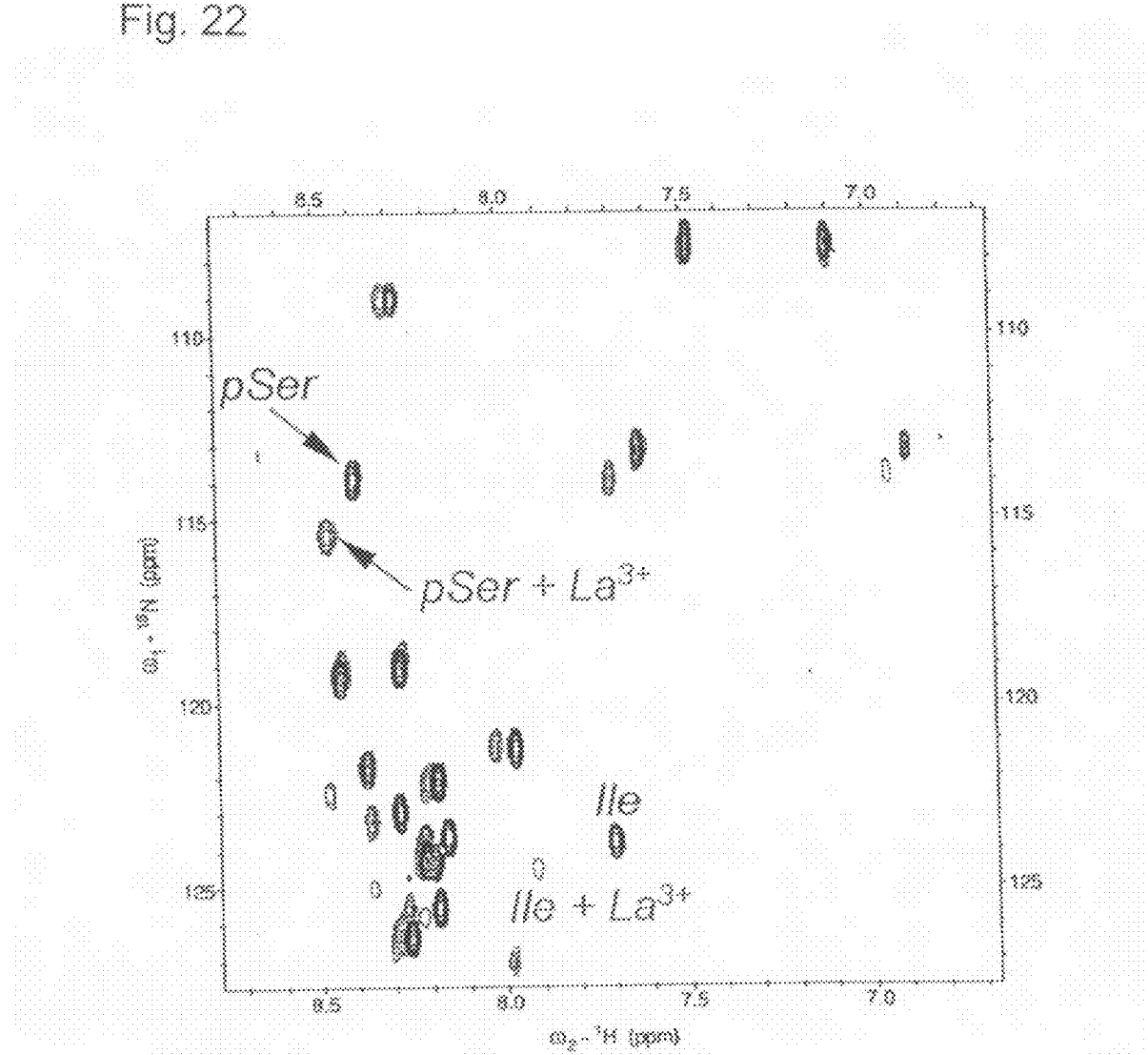
FIG. 22. $^1H$-$^{15}N$ HSQC spectra of phosphorylated pKID-PKC in the absence of metal (dark) and in the presence of $La^{3+}$ (light). Large changes were observed for the amide resonances of phosphoserine and of Ile8, which is conjugated to the Trp7 carbonyl that contacts metal in an EF hand.
Figure 23:
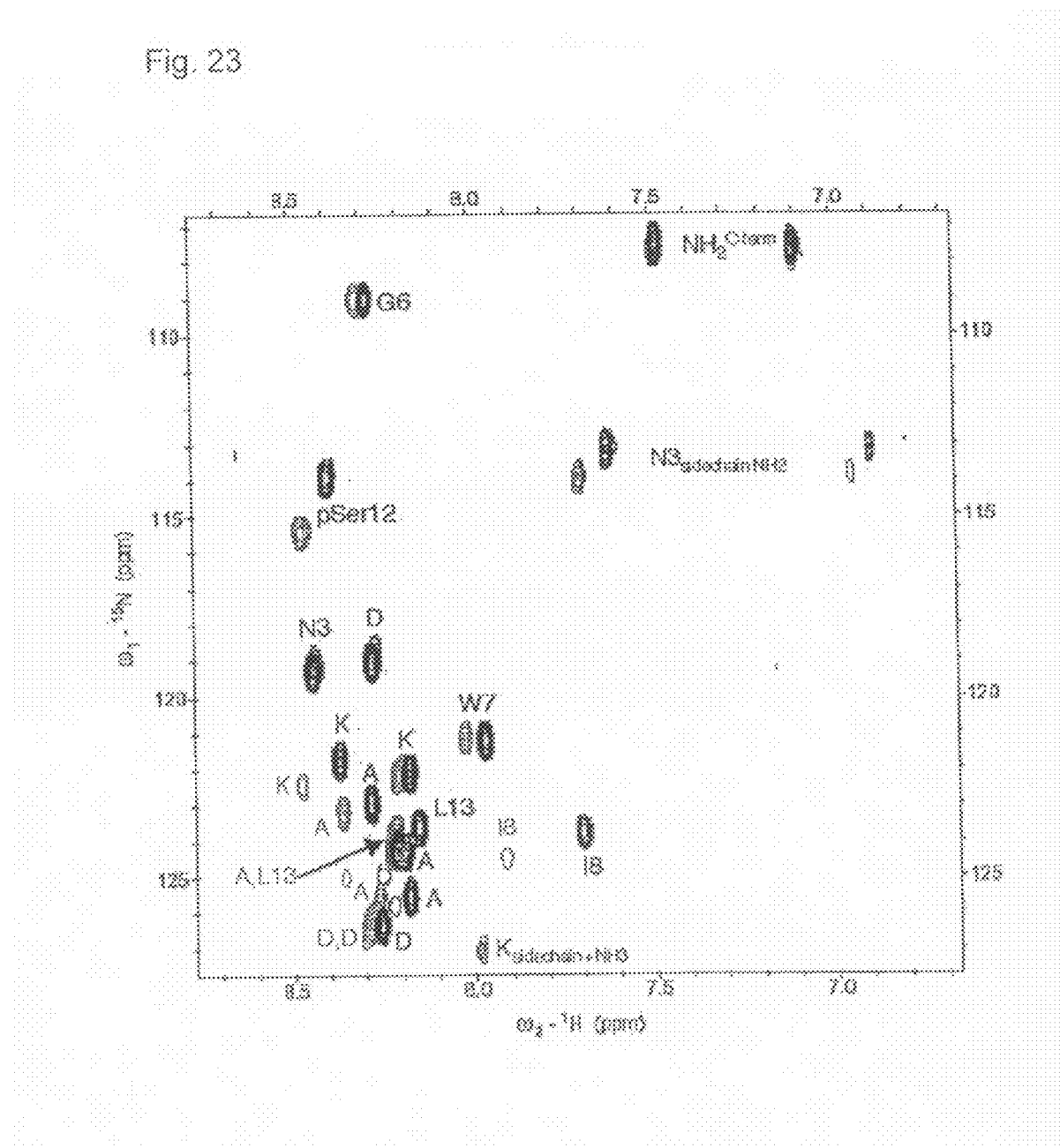
FIG. 23. $^1H$-$^{15}N$ HSQC spectra of 1.5 mM phosphorylated pKID-PKC in the absence (dark contours) and presence (light contours) of 1.5 mM $La^{3+}$. Peaks were assigned based on TOCSY data. Significant changes in chemical shift were observed for residues expected to be directly involved in metal binding in an EF hand, including the phosphoserine amide; the Ile8 amide, which is conjugated to the Trp7 main chain carbonyl that contacts metal in a canonical EF hand; and the Asn3 side chain amide.

Addition of paramagnetic $Tb^{3+}$ to phosphorylated pKID-PKC resulted in the disappearance of most signals, consistent with pKID-PKC-$Tb^{3+}$ complex formation and $Tb^{3+}$-induced paramagnetic relaxation. $^1H$-$^{15}N$ HSQC spectra (see FIG. 22, FIG. 23) of phosphorylated pKID-PKC in the absence and in the presence of diamagnetic $La^{3+}$ indicated that the metal induced significant changes in chemical shifts, particularly for metal-binding residues, consistent with peptide-metal complex formation.

REFERENCES

[1] Manning G et al., Science 298:1912-34 (2002).
[2] Bridges A J, Chem. Rev. 101:2541-71 (2001).
[3] Szilak L et al., Protein Sci. 6:1273-83 (1997).
[4] Szilak L et al., Nat. Struct. Biol. 4:112-14 (1997).
[5] Signarvic R S & DeGrado W F, J. Mol. Biol. 334:1-12 (2003).
[6] Davis B G, Science 303:480-82 (2004).
[7] Babu Y S et al., Nature 315:37-40 (1985).
[8] Meador W E et al., Science 257:1251-55 (1992).
[9] Kuboniwa H et al., Nat. Struct. Biol. 2:768-76 (1995).
[10] Wang C L et al., Biochemistry 20:2439-44 (1981).
[11] Gariepy J et al., Biochemistry 22:1765-72 (1983).
[12] Macmanus J P et al., J. Biol. Chem. 265:10358-66 (1990).
[13] Siedlecka M et al., Proc. Natl. Acad. Sci. USA 96:903-08 (1999).
[14] Franz K J et al., ChemBioChem 4:265-71 (2003).
[15] Nitz M et al., ChemBioChem 4:272-76 (2003).
[16] Nitz M et al., Agnew. Chem. Int. Ed. 43:3682-85 (2004).
[17] Selvin P R, Ann. Rev. Biophys. Biomol. Struct. 31:275-302 (2002).
[18] Barbieri R et al., J. Am. Chem. Soc. 124:5581-87 (2002).
[19] Wohnert J et al., J. Am. Chem. Soc. 125:13338-39 (2003).
[20] Kovacic R T et al., J. Am. Chem. Soc. 125:6656-62 (2003).
[21] Pearson R B & Kemp B E, Meth. Enzymol. 200:62-81 (1991).
[22] Lee V H L, "Peptide and Protein Drug Delivery", New York, N.Y., M. Dekker (1990).
[23] Ausubel F M et al., "Current Protocols in Molecular Biology", John Wiley (1987-1998).
[24] Sambrook J et al., "Molecular Cloning, A Laboratory Manual", 2d Edition, Cold Spring Harbor Laboratory Press (1989).
[25] Jones J D et al., EMBO J. 4:2411-18 (1985).
[26] Almeida E R P et al., Mol. Gen. Genet. 218:78-86 (1989).
[27] Keegstra K, Cell 56:247-53 (1989).
[28] Chrispeels M J, Annu. Rev. Plant Physiol. Plant Mol. Biol. 42:21-53 (1991).
[29] Raikhel N, Plant Physiol. 100:1627-1632 (1992).
[30] Rothman D M et al., Trends Cell Biol. 15:502-10 (2005).
[31] Wright D et al., Proc. Natl. Acad. Sci. USA 78:6048-50 (1981).
[32] Ng T et al., Science 283:2085-89 (1999).
[33] Cotton G J & Muir T W, Chem. Biol. 7:253-61 (2000).
[34] Nagai Y et al., Nat. Biotechnol. 18:313-16 (2000).
[35] Zhang J et al., Proc. Natl. Acad. Sci. USA 98:14997-15002 (2001).
[36] Ting A Y et al., Proc. Natl. Acad. Sci. USA 98:15003-08 (2001).
[37] Sato M et al., Nat. Biotechnol. 20:287-94 (2002).
[38] Yeh R H et al., J. Biol. Chem. 277:11527-32 (2002).
[39] Chen C A et al., J. Am. Chem. Soc. 124:3840-41 (2002).
[40] Ojida A et al., J. Am. Chem. Soc. 124:6256-58 (2002).
[41] Veldhuyzen W F et al., J. Am. Chem. Soc. 125:13358-59 (2003).
[42] Shults M D & Imperiali B, J. Am. Chem. Soc. 125:14248-49 (2003).
[43] Schleifenbaum A et al., J. Am. Chem. Soc. 126:11786-87 (2004).
[44] Shults M D et al., Nat. Methods 2:277-83 (2005).
[45] Wang Q & Lawrence D S, J. Am. Chem. Soc. 127:7684-85 (2005)
[46] Nelson M R & Chazin W J, Biometals 11:297-318 (1998)
[47] Rigden D J & Galperin M Y, J. Mol. Biol. 343:971-84 (2004)
[48] Caravan P et al., Chem. Commun. 2574-2575 (2003)

We claim:

1. A method of producing a kinase/phosphatase inducible domain comprising:
   (a) replacing a structurally significant glutamic acid or aspartic acid residue in an EF hand domain with a replacement serine or threonine residue, said EF hand domain having the formula:

$X^1X^2DX^3X^4X^5DX^6WX^7X^8X^9X^{10}X^{11}X^{12}X^{13}X^{14}X^{15}X^{16}$ wherein $X^1$ is an optionally present amino acid;
   $X^2$ is an optionally present amino acid;
   $X^3$ is K, A, or L;
   $X^4$ is N or D;
   $X^5$ is A or G;
   $X^6$ is G or R;
   $X^7$ is I or R;
   $X^8$ is D, R, S, or T;
   $X^9$ is A, R, K, P, or F;
   $X^{10}$ is an optionally present A, R, G, or L, provided that, when $X^8$ is not S or T, $X^{10}$ is present;
   $X^{11}$ is an optionally present S, T, or R, provided that, when $X^8$ is not S or T, $X^{11}$ is present and is S or T;
   $X^{12}$ is an optionally present L, P, I, K, or F;
   $X^{13}$ is an optionally present K, A, I, R, G, or L;
   $X^{14}$ is an optionally present A, R, or P;
   $X^{15}$ is an optionally present K;
   $X^{16}$ is an optionally present A; and
   (b) optionally, activating the EF hand domain comprising the replacement serine or threonine residue by phosphorylating the replacement serine or threonine residue.

2. The method of claim 1, wherein the structurally significant glutamic acid or aspartic acid residue is a metal-binding glutamic acid or aspartic acid.

3. The method of claim 1, wherein the EF hand domain has the amino acid sequence set forth in SEQ ID NO:1, SEQ ID NO:3, SEQ ID NO:5, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:40, SEQ ID NO:41, SEQ ID NO:34, SEQ ID NO:35, SEQ ID NO:36, SEQ ID NO:37, SEQ ID NO:38, or SEQ ID NO:39.

4. The method of claim 1, wherein the kinase is protein kinase A, protein kinase C, Erk, Akt, Pim1, AMPK, glycogen synthase kinase, or cdk5.

5. The method of claim 1 comprising after step (b) the further step of deactivating the domain comprising the replacement serine or threonine residue by dephosphorylating the phosphorylated serine or threonine residue.

* * * * *

SEQUENCE LISTING

<160> NUMBER OF SEQ ID NOS: 41

<210> SEQ ID NO 1
<211> LENGTH: 14
<212> TYPE: PRT
<213> ORGANISM: Artificial
<220> FEATURE:
<223> OTHER INFORMATION: EF Hand Domain

<400> SEQUENCE: 1

Asp Lys Asn Ala Asp Gly Trp Ile Asp Arg Ala Ser Leu Ala
1               5                   10

<210> SEQ ID NO 2
<211> LENGTH: 14
<212> TYPE: PRT
<213> ORGANISM: Artificial
<220> FEATURE:
<223> OTHER INFORMATION: EF Hand Domain
<220> FEATURE:
<221> NAME/KEY: MOD_RES
<222> LOCATION: (12)..(12)
<223> OTHER INFORMATION: PHOSPHORYLATION

<400> SEQUENCE: 2

Asp Lys Asn Ala Asp Gly Trp Ile Asp Arg Ala Ser Leu Ala
1               5                   10

<210> SEQ ID NO 3
<211> LENGTH: 14
<212> TYPE: PRT
<213> ORGANISM: Artificial
<220> FEATURE:
<223> OTHER INFORMATION: EF Hand Domain

<400> SEQUENCE: 3

Asp Lys Asn Ala Asp Gly Trp Ile Asp Ala Ala Ser Leu Lys
1               5                   10

<210> SEQ ID NO 4
<211> LENGTH: 14
<212> TYPE: PRT
<213> ORGANISM: Artificial
<220> FEATURE:
<223> OTHER INFORMATION: EF Hand Domain
<220> FEATURE:
<221> NAME/KEY: MOD_RES
<222> LOCATION: (12)..(12)
<223> OTHER INFORMATION: PHOSPHORYLATION

<400> SEQUENCE: 4

Asp Lys Asn Ala Asp Gly Trp Ile Asp Ala Ala Ser Leu Lys
1               5                   10

<210> SEQ ID NO 5
<211> LENGTH: 14
<212> TYPE: PRT
<213> ORGANISM: Artificial
<220> FEATURE:
<223> OTHER INFORMATION: EF Hand Domain

<400> SEQUENCE: 5

Asp Lys Asn Ala Asp Gly Trp Ile Asp Ala Ala Ser Pro Ala
1               5                   10

<210> SEQ ID NO 6

-continued

```
<211> LENGTH: 14
<212> TYPE: PRT
<213> ORGANISM: Artificial
<220> FEATURE:
<223> OTHER INFORMATION: EF Hand Domain
<220> FEATURE:
<221> NAME/KEY: MOD_RES
<222> LOCATION: (12)..(12)
<223> OTHER INFORMATION: PHOSPHORYLATION

<400> SEQUENCE: 6

Asp Lys Asn Ala Asp Gly Trp Ile Asp Ala Ala Ser Pro Ala
1               5                   10

<210> SEQ ID NO 7
<211> LENGTH: 14
<212> TYPE: PRT
<213> ORGANISM: Artificial
<220> FEATURE:
<223> OTHER INFORMATION: Consensus EF Hand Domain

<400> SEQUENCE: 7

Asp Lys Asn Ala Asp Gly Tyr Ile Asp Ala Ala Glu Leu Lys
1               5                   10

<210> SEQ ID NO 8
<211> LENGTH: 16
<212> TYPE: PRT
<213> ORGANISM: Artificial
<220> FEATURE:
<223> OTHER INFORMATION: EF Hand Domain

<400> SEQUENCE: 8

Asp Lys Asn Ala Asp Gly Trp Ile Asp Arg Arg Ser Ile Ile Ala Lys
1               5                   10                  15

<210> SEQ ID NO 9
<211> LENGTH: 16
<212> TYPE: PRT
<213> ORGANISM: Artificial
<220> FEATURE:
<223> OTHER INFORMATION: EF Hand Domain

<400> SEQUENCE: 9

Asp Lys Asn Ala Asp Gly Trp Ile Arg Arg Arg Ser Ile Ile Ala Lys
1               5                   10                  15

<210> SEQ ID NO 10
<211> LENGTH: 16
<212> TYPE: PRT
<213> ORGANISM: Artificial
<220> FEATURE:
<223> OTHER INFORMATION: EF Hand Domain

<400> SEQUENCE: 10

Asp Ala Asp Ala Asp Gly Trp Ile Arg Arg Arg Ser Ile Ile Ala Lys
1               5                   10                  15

<210> SEQ ID NO 11
<211> LENGTH: 16
<212> TYPE: PRT
<213> ORGANISM: Artificial
<220> FEATURE:
<223> OTHER INFORMATION: EF Hand Domain

<400> SEQUENCE: 11

Asp Ala Asn Ala Asp Gly Trp Ile Arg Arg Arg Ser Ile Ile Ala Lys
1               5                   10                  15
```

```
<210> SEQ ID NO 12
<211> LENGTH: 16
<212> TYPE: PRT
<213> ORGANISM: Artificial
<220> FEATURE:
<223> OTHER INFORMATION: EF Hand Domain

<400> SEQUENCE: 12

Asp Ala Asn Ala Asp Gly Trp Ile Arg Arg Ala Ser Ile Ile Ala Lys
 1               5                  10                  15

<210> SEQ ID NO 13
<211> LENGTH: 16
<212> TYPE: PRT
<213> ORGANISM: Artificial
<220> FEATURE:
<223> OTHER INFORMATION: EF Hand Domain

<400> SEQUENCE: 13

Asp Ala Asp Ala Asp Gly Trp Ile Lys Lys Ala Ser Ile Ile Ala Lys
 1               5                  10                  15

<210> SEQ ID NO 14
<211> LENGTH: 16
<212> TYPE: PRT
<213> ORGANISM: Artificial
<220> FEATURE:
<223> OTHER INFORMATION: EF Hand Domain

<400> SEQUENCE: 14

Asp Ala Asp Ala Asp Gly Trp Ile Arg Arg Ala Ser Ile Ile Ala Lys
 1               5                  10                  15

<210> SEQ ID NO 15
<211> LENGTH: 16
<212> TYPE: PRT
<213> ORGANISM: Artificial
<220> FEATURE:
<223> OTHER INFORMATION: EF Hand Domain

<400> SEQUENCE: 15

Asp Lys Asp Ala Asp Gly Trp Ile Arg Arg Ala Ser Ile Ile Ala Lys
 1               5                  10                  15

<210> SEQ ID NO 16
<211> LENGTH: 16
<212> TYPE: PRT
<213> ORGANISM: Artificial
<220> FEATURE:
<223> OTHER INFORMATION: EF Hand Domain

<400> SEQUENCE: 16

Asp Ala Asp Ala Asp Gly Trp Arg Ser Arg Arg Ser Ile Ile Ala Lys
 1               5                  10                  15

<210> SEQ ID NO 17
<211> LENGTH: 17
<212> TYPE: PRT
<213> ORGANISM: Artificial
<220> FEATURE:
<223> OTHER INFORMATION: EF Hand Domain

<400> SEQUENCE: 17

Asp Lys Asn Ala Asp Gly Trp Ile Ser Arg Gly Ser Phe Arg Arg Lys
 1               5                  10                  15
```

Ala

```
<210> SEQ ID NO 18
<211> LENGTH: 16
<212> TYPE: PRT
<213> ORGANISM: Artificial
<220> FEATURE:
<223> OTHER INFORMATION: EF Hand Domain

<400> SEQUENCE: 18

Asp Lys Asn Ala Asp Gly Trp Ile Ser Pro Leu Ser Pro Gly Pro Lys
1               5                   10                  15

<210> SEQ ID NO 19
<211> LENGTH: 18
<212> TYPE: PRT
<213> ORGANISM: Artificial
<220> FEATURE:
<223> OTHER INFORMATION: EF Hand Domain

<400> SEQUENCE: 19

Tyr Ile Asp Lys Asp Ala Asp Gly Trp Ile Arg Arg Ala Ser Ile Ile
1               5                   10                  15

Ala Lys

<210> SEQ ID NO 20
<211> LENGTH: 18
<212> TYPE: PRT
<213> ORGANISM: Artificial
<220> FEATURE:
<223> OTHER INFORMATION: EF Hand Domain

<400> SEQUENCE: 20

Tyr Ile Asp Lys Asp Ala Asp Gly Trp Ile Arg Arg Ala Ser Leu Leu
1               5                   10                  15

Ala Lys

<210> SEQ ID NO 21
<211> LENGTH: 18
<212> TYPE: PRT
<213> ORGANISM: Artificial
<220> FEATURE:
<223> OTHER INFORMATION: EF Hand Domain

<400> SEQUENCE: 21

Trp Ile Asp Lys Asp Ala Asp Gly Trp Ile Arg Arg Ala Ser Leu Leu
1               5                   10                  15

Ala Lys

<210> SEQ ID NO 22
<211> LENGTH: 17
<212> TYPE: PRT
<213> ORGANISM: Artificial
<220> FEATURE:
<223> OTHER INFORMATION: EF Hand Domain

<400> SEQUENCE: 22

Asp Lys Asp Ala Asp Gly Trp Ile Ser Arg Gly Ser Phe Arg Arg Lys
1               5                   10                  15

Ala

<210> SEQ ID NO 23
<211> LENGTH: 19
<212> TYPE: PRT
```

```
<213> ORGANISM: Artificial
<220> FEATURE:
<223> OTHER INFORMATION: EF Hand Domain

<400> SEQUENCE: 23

Tyr Ile Asp Lys Asp Ala Asp Gly Trp Ile Ser Arg Gly Ser Phe Arg
1               5                   10                  15

Arg Lys Ala

<210> SEQ ID NO 24
<211> LENGTH: 19
<212> TYPE: PRT
<213> ORGANISM: Artificial
<220> FEATURE:
<223> OTHER INFORMATION: EF Hand Domain

<400> SEQUENCE: 24

Trp Ile Asp Lys Asp Ala Asp Gly Trp Ile Ser Arg Gly Ser Phe Arg
1               5                   10                  15

Arg Lys Ala

<210> SEQ ID NO 25
<211> LENGTH: 16
<212> TYPE: PRT
<213> ORGANISM: Artificial
<220> FEATURE:
<223> OTHER INFORMATION: EF Hand Domain

<400> SEQUENCE: 25

Asp Lys Asp Ala Asp Gly Trp Ile Ser Pro Leu Ser Pro Gly Pro Lys
1               5                   10                  15

<210> SEQ ID NO 26
<211> LENGTH: 18
<212> TYPE: PRT
<213> ORGANISM: Artificial
<220> FEATURE:
<223> OTHER INFORMATION: EF Hand Domain

<400> SEQUENCE: 26

Tyr Ile Asp Lys Asp Ala Asp Gly Trp Ile Ser Pro Leu Ser Pro Gly
1               5                   10                  15

Pro Lys

<210> SEQ ID NO 27
<211> LENGTH: 18
<212> TYPE: PRT
<213> ORGANISM: Artificial
<220> FEATURE:
<223> OTHER INFORMATION: EF Hand Domain

<400> SEQUENCE: 27

Trp Ile Asp Lys Asp Ala Asp Gly Trp Ile Ser Pro Leu Ser Pro Gly
1               5                   10                  15

Pro Lys

<210> SEQ ID NO 28
<211> LENGTH: 16
<212> TYPE: PRT
<213> ORGANISM: Artificial
<220> FEATURE:
<223> OTHER INFORMATION: EF Hand Domain

<400> SEQUENCE: 28
```

```
Asp Ala Asp Ala Asp Gly Trp Ile Ser Arg Arg Ser Ile Ile Ala Lys
1               5                   10                  15
```

<210> SEQ ID NO 29
<211> LENGTH: 14
<212> TYPE: PRT
<213> ORGANISM: Artificial
<220> FEATURE:
<223> OTHER INFORMATION: EF Hand Domain

<400> SEQUENCE: 29

```
Asp Leu Asn Ala Asp Gly Trp Ile Ser Phe Arg Arg Lys Ala
1               5                   10
```

<210> SEQ ID NO 30
<211> LENGTH: 14
<212> TYPE: PRT
<213> ORGANISM: Artificial
<220> FEATURE:
<223> OTHER INFORMATION: EF Hand Domain

<400> SEQUENCE: 30

```
Asp Leu Asn Ala Asp Gly Trp Ile Thr Ala Ala Thr Ala Lys
1               5                   10
```

<210> SEQ ID NO 31
<211> LENGTH: 14
<212> TYPE: PRT
<213> ORGANISM: Artificial
<220> FEATURE:
<223> OTHER INFORMATION: EF Hand Domain

<400> SEQUENCE: 31

```
Asp Leu Asn Ala Asp Gly Trp Ile Thr Ala Ala Thr Ala Lys
1               5                   10
```

<210> SEQ ID NO 32
<211> LENGTH: 9
<212> TYPE: PRT
<213> ORGANISM: Artificial
<220> FEATURE:
<223> OTHER INFORMATION: EF Hand Domain

<400> SEQUENCE: 32

```
Asp Leu Asn Ala Asp Gly Trp Ile Thr
1               5
```

<210> SEQ ID NO 33
<211> LENGTH: 17
<212> TYPE: PRT
<213> ORGANISM: Artificial
<220> FEATURE:
<223> OTHER INFORMATION: EF Hand Domain

<400> SEQUENCE: 33

```
Asp Lys Asp Ala Asp Gly Trp Ile Arg Arg Ser Ser Trp Arg Val Val
1               5                   10                  15

Ser
```

<210> SEQ ID NO 34
<211> LENGTH: 17
<212> TYPE: PRT
<213> ORGANISM: Artificial
<220> FEATURE:
<223> OTHER INFORMATION: EF Hand Domain

<400> SEQUENCE: 34

```
Asp Lys Asp Ala Asp Gly Trp Ile Arg Arg Ser Thr Trp Arg Val Val
1               5                   10                  15

Ser
```

<210> SEQ ID NO 35
<211> LENGTH: 16
<212> TYPE: PRT
<213> ORGANISM: Artificial
<220> FEATURE:
<223> OTHER INFORMATION: EF Hand Domain

<400> SEQUENCE: 35

```
Asp Lys Asp Ala Asp Gly Trp Arg Ser Ser Met Ser Phe Ala Ser Asn
1               5                   10                  15
```

<210> SEQ ID NO 36
<211> LENGTH: 9
<212> TYPE: PRT
<213> ORGANISM: Artificial
<220> FEATURE:
<223> OTHER INFORMATION: EF Hand Domain

<400> SEQUENCE: 36

```
Asp Lys Asp Ala Asp Gly Trp Ile Ser
1               5
```

<210> SEQ ID NO 37
<211> LENGTH: 14
<212> TYPE: PRT
<213> ORGANISM: Artificial
<220> FEATURE:
<223> OTHER INFORMATION: EF Hand Domain

<400> SEQUENCE: 37

```
Asp Lys Asp Ala Asp Gly Trp Ile Thr Phe Arg Arg Lys Ala
1               5                   10
```

<210> SEQ ID NO 38
<211> LENGTH: 13
<212> TYPE: PRT
<213> ORGANISM: Artificial
<220> FEATURE:
<223> OTHER INFORMATION: EF Hand Domain

<400> SEQUENCE: 38

```
Asp Lys Asp Gly Asp Arg Trp Ile Ser Ile Ile Ala Lys
1               5                   10
```

<210> SEQ ID NO 39
<211> LENGTH: 13
<212> TYPE: PRT
<213> ORGANISM: Artificial
<220> FEATURE:
<223> OTHER INFORMATION: EF Hand Domain

<400> SEQUENCE: 39

```
Asp Lys Asp Ala Asp Arg Trp Arg Ser Ile Ile Ala Lys
1               5                   10
```

<210> SEQ ID NO 40
<211> LENGTH: 20
<212> TYPE: PRT
<213> ORGANISM: Artificial
<220> FEATURE:
<223> OTHER INFORMATION: EF Hand Domain
<220> FEATURE:

```
<221> NAME/KEY: MOD_RES
<222> LOCATION: (16)..(16)
<223> OTHER INFORMATION: PHOSPHORYLATION

<400> SEQUENCE: 40

Asp Lys Asp Ala Asp Gly Trp Ile Ser Pro Arg Ala Arg Ser Asn Ser
1               5                   10                  15

Trp Ser Lys Gln
            20

<210> SEQ ID NO 41
<211> LENGTH: 20
<212> TYPE: PRT
<213> ORGANISM: Artificial
<220> FEATURE:
<223> OTHER INFORMATION: EF Hand Domain
<220> FEATURE:
<221> NAME/KEY: MOD_RES
<222> LOCATION: (16)..(16)
<223> OTHER INFORMATION: PHOSPHORYLATION

<400> SEQUENCE: 41

Asp Lys Asp Ala Asp Gly Trp Ile Ser Pro Arg Ala Arg His Ala Ser
1               5                   10                  15

Gly Ala Gln Ala
            20
```